United States Patent
Chalmers

(10) Patent No.: US 8,909,346 B2
(45) Date of Patent: Dec. 9, 2014

(54) FREQUENCY SPECIFIC MICOCURRENT FOR TREATMENT OF DENTAL INDICATIONS

(76) Inventor: Mary Ellen S. Chalmers, Santa Rosa, CA (US)

(*) Notice: Subject to any disclaimer, the term of this patent is extended or adjusted under 35 U.S.C. 154(b) by 1103 days.

(21) Appl. No.: 12/378,675

(22) Filed: Feb. 17, 2009

(65) Prior Publication Data

US 2010/0082027 A1   Apr. 1, 2010

Related U.S. Application Data

(60) Provisional application No. 61/065,904, filed on Feb. 15, 2008.

(51) Int. Cl.
| | |
|---|---|
| *A61N 1/00* | (2006.01) |
| *A61N 1/36* | (2006.01) |
| *A61C 19/06* | (2006.01) |
| *A61N 1/05* | (2006.01) |
| *A61N 1/20* | (2006.01) |

(52) U.S. Cl.
CPC .............. *A61N 1/36021* (2013.01); *A61C 19/06* (2013.01); *A61N 1/0548* (2013.01); *A61N 1/205* (2013.01)
USPC ...................................... 607/47; 607/2; 607/1

(58) Field of Classification Search
CPC ........... A61N 1/36021; A61N 1/36014; A61N 1/36017; A61N 1/0548
USPC .......................................................... 607/47
See application file for complete search history.

(56) References Cited

U.S. PATENT DOCUMENTS

| | | | | |
|---|---|---|---|---|
| 4,782,837 A | * | 11/1988 | Hogan ............................ | 607/47 |
| 4,784,142 A | * | 11/1988 | Liss et al. ........................ | 607/47 |
| 4,924,880 A | * | 5/1990 | O'Neill et al. .................. | 607/47 |
| 5,018,525 A | * | 5/1991 | Konobevtsev et al. ......... | 607/47 |
| 2003/0018367 A1 | * | 1/2003 | DiLorenzo ...................... | 607/46 |

FOREIGN PATENT DOCUMENTS

| | | | |
|---|---|---|---|
| WO | WO 01/03768 A1 | 1/2001 | |
| WO | WO 2005/077452 A1 | 8/2005 | |
| WO | WO 2008/145724 A1 | 12/2008 | |
| WO | WO 2008145724 A1 * | 12/2008 | ............... A61N 1/34 |

OTHER PUBLICATIONS

McMakin, C., Microcurrent Treatment of Myofascial Pain in the Head, Neck, and Face, Top. Clin. Chiro., 1998, pp. 29-35, vol. 5, No. 1, Aspen Pub., Inc.
McMakin, C.R., Microcurrent therapy: a novel treatment method for chronic low back myofascial pain, Jour. Bodywork & Movement Therapies, 2004, pp. 143-153, vol. 8, Elsevier.
McMakin, C.R., et al., Cytokine changes with microcurrent treatment of fibromyalgia, etc., Jour. Bodywork & Movement Therapoes, 2005, pp. 169-176, vol. 9, Elsevier Ltd.
Extended European search report, European Application No. 10153892.4-2305, Jul. 15, 2010.

* cited by examiner

*Primary Examiner* — Christopher D Koharski
*Assistant Examiner* — Philip Edwards
(74) *Attorney, Agent, or Firm* — William C. Milks, III

(57) ABSTRACT

Protocols are provided for the use of frequency specific microcurrent in conjunction with dental or orthodontic procedures to treat or prevent inflammation induced complications. Specific protocols are disclosed for use in conjunction with gingival surgery and chronic periodontitis, implant/osseous periodontal surgery, general post operative trauma, pulpal trauma, pulpal inflammation, root canal post op, chronic osteonecrosis, osteonecrosis surgery post op, orthodontic pain prevention, and orthodontic mid-adjustment procedures.

23 Claims, 4 Drawing Sheets

Results of *TOPAS* GCF Toxicity Prescreening Assay

Patient Name: __PATIENT X__    Date: __11/26/07__

Sample Type: C = Control, E = Endo, N = Non-Vital, P = Perio, I = Implant, O = Other

| Colorimeter OD Reading | Toxin Level Detected | Toxin Level | Colorimeter OD Reading | Protein Level Detected | Protein Level |
|---|---|---|---|---|---|
| <0.05 | Normal | 1 | <0.05 | Normal | A |
| 0.05-0.10 | Low | 2 | 0.05-0.15 | Low | B |
| 0.11-0.20 | Moderate | 3 | 0.16-0.25 | Moderate | C |
| >0.20 | High | 4 | >0.25 | High | D |

| Tooth Number | #22 | Sample Type | Control |
|---|---|---|---|
| Toxin Reading | .17 | Protein Reading | .15 |

| Tooth Number | #19 | Sample Type | ENDO |
|---|---|---|---|
| Toxin Reading | .44 | Protein Reading | .32 |

| Tooth Number | #19 | Sample Type | ENDO |
|---|---|---|---|
| Toxin Reading | .10 | Protein Reading | .17 |

| Tooth Number | | Sample Type | |
|---|---|---|---|
| Toxin Reading | | Protein Reading | |

| Tooth Number | | Sample Type | |
|---|---|---|---|
| Toxin Reading | | Protein Reading | |

| Tooth Number | | Sample Type | |
|---|---|---|---|
| Toxin Reading | | Protein Reading | |

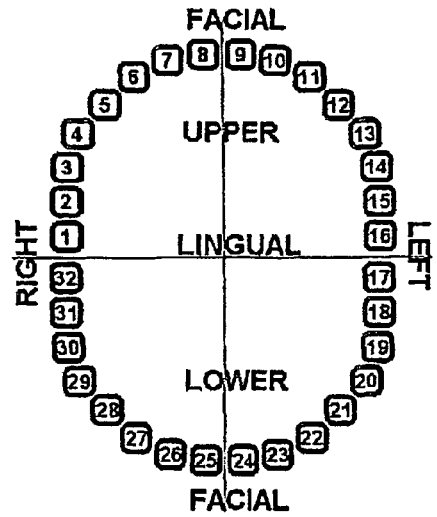

Soak Level: ⊔⊔⊔⊔

Comments: _____

FIG. 6

FREQUENCY SPECIFIC MICOCURRENT FOR TREATMENT OF DENTAL INDICATIONS

CROSS-REFERENCE TO RELATED PATENT APPLICATION

This application relates to U.S. Provisional Patent Application No. 61/065,904 filed on Feb. 15, 2008, entitled FREQUENCY SPECIFIC MICOCURRENT FOR TREATMENT OF DENTAL INDICATIONS, which is hereby incorporated herein in its entirety by this reference.

BACKGROUND OF THE INVENTION

1. Field of the Invention

The present invention relates to apparatus and processes for producing electrical stimuli and, more particularly, to variable frequency, low current devices and techniques for applying electrical stimuli to the human body. Specifically, one preferred embodiment of the present invention provides a variable frequency microcurrent device and method for producing electrical stimuli according to protocols developed to treat dental indications, for example, inflammation, associated with oral surgery or other dental or orthodontic procedures.

2. Description of the Prior Art

The application of electrical stimuli to treat pain and other medical indications such as disease or infection is known. The application of electrical stimuli in the case of abscessed or impacted teeth and canker sores is also known. Moreover, the treatment of pain in the temporomandibular joint (TMJ) would be a logical extension of the application of electrical stimuli to treat other common types of pain. However, the application of electrical stimuli in conjunction with performing oral surgery or other dental or orthodontic procedures has not heretofore been known.

Furthermore, the application of electrical stimuli in the context of addressing fundamental causes to dental disease does not appear to have been investigated. In adopting a systemic approach to dentistry, inflammation and its role in dental problems becomes an important factor. There is evidence that inflammation and disease in the mouth can have a significant impact on the health of the remainder of the human body.

It is communicated increasingly in dental literature that there is a systemic link between periodontal disease and cardiovascular disease. *Grand Rounds in Oral Systemic Medicine*, Volume 2, Number 3, September 2007, in the "Report of the Scottsdale Project," Grand Rounds Supplement, pages 8-9, in FIG. 2, http://www.grandrounds-digital.com/grandrounds/200709/, explains one hypothesis for the connection. Oral flora forms a subgingival biofilm. Endotoxins, enzymes, and metabolic by products produced by the gram negative bacteria enter the blood stream triggering a host immune response. That immune response leads to the accumulation of inflammatory cells and the production of proinflammatory cytokines, specifically Interleukin-I and tissue necrosis factor Alpha.

An article appeared in the *Journal of Endodontics* in February of 2006 reporting an evaluation of pulpal inflammation and the incidence of coronary heart disease. The results reported in the article suggested a possible association between the number of root canals a patient had and coronary artery disease. See, Kaumudi J. Joshipura ScD, Waranuch Pitiphat ScD, Hsin-Chia Hung ScD, Walter C. Willett DrPH, Graham A. Colditz ScD, and Chester W. Douglass PhD, "Pulpal Inflammation and Incidence of Coronary Heart Disease," *Journal of Endodontics*, Volume 32, Issue 2, February 2006, Pages 99-103.

Additionally, Jeffery S. Bland, PhD, FACN, CNS in his annual seminar in February, 2007 spoke at length about the link between inflammation and insulin resistance, and the vicious cycle that arises: when a diabetic patient has inflammation, he or she has more insulin resistance, and when the patient has more insulin resistance, it triggers more inflammation. It has been reported that treating periodontal disease in diabetic patients affords them better blood sugar control. As evidence, some periodontists evaluate control of periodontal disease by an HbA1c blood test, which reveals average blood glucose over a period of two to three months.

In the mouth where there are many types of microorganisms, the presence or absence of inflammation can mean the difference between health and disease, infection or no infection. Dr. Erica Steffe, the head of infectious diseases at Santa Rosa Memorial Hospital, located in Santa Rosa, Calif., generally believes that within the body there is a very fine line between an organ being merely inflamed and an organ being inflamed and infected. In addition, she believes that the presence of chronic inflammation in an organ causes that organ to be much more susceptible to infection.

Complications may arise in dental patients who undergo oral surgery or dental procedures, and inflammation is frequently symptomatic of these complications. The present invention addresses common dental maladies from an inflammatory perspective. The various embodiments of the present invention overcome dental problems related to inflammation through the application of frequency specific microcurrent protocols that treat inflammation and/or other symptoms such as pain.

SUMMARY OF THE INVENTION

In accordance with one aspect of the present invention, it is recognized that in the mouth where there are many types of microorganisms, the presence or absence of inflammation can mean the difference between health and disease, infection or no infection. With respect to dentistry, controlling inflammation is paramount, and in accordance with one aspect of the present invention, frequency specific microcurrent is used as a viable modality to address inflammation. By addressing the inflammation, one can prevent as well as treat dental disease.

Considered in more detail, the use of frequency specific microcurrent therapy controlling oral inflammation has been demonstrated to be an important procedure that a dentist can perform on a patient. There is increasing evidence that bacteria are secondary to inflammation in the propagation of dental disease. This particular observation is critical in the case of the mouth, because of both the high number and the wide variety of bacteria and pathogens that exist within the mouth. Based on the theory that inflammation predisposes an organism to infection, then eradicating inflammation dramatically decreases the likelihood of disease. Because frequency specific microcurrent has the capability to address inflammation, harnessing that capability for the control of periodontal disease locally, for example, will have positive effects systemically.

If an ultimate goal in addressing dental disease is the elimination of oral inflammation, rather than to merely fix teeth, the approach to dental care and treatment becomes dramatically different. In accordance with the various embodiments of the present invention, frequency specific microcurrent therapy using various protocols has the significant advantage of eliminating inflammation and the complications that may ensue.

The foregoing and other objects, features, and advantages of the present invention will become more readily apparent from the following detailed description of various embodiments of the present invention, which proceeds with reference to the accompanying drawing.

BRIEF DESCRIPTION OF THE DRAWING

The various embodiments of the present invention will be described in conjunction with the accompanying figures of the drawing to facilitate an understanding of the present invention. In the figures, like reference numerals refer to like elements. In the drawing:

FIG. 6 shows results of a TOPAS GCF toxicity prescreening assay following a root canal performed in conjunction with using the root canal post op protocol in accordance with one embodiment of the present invention.

DETAILED DESCRIPTION OF THE PREFERRED EMBODIMENTS

Figure 1:
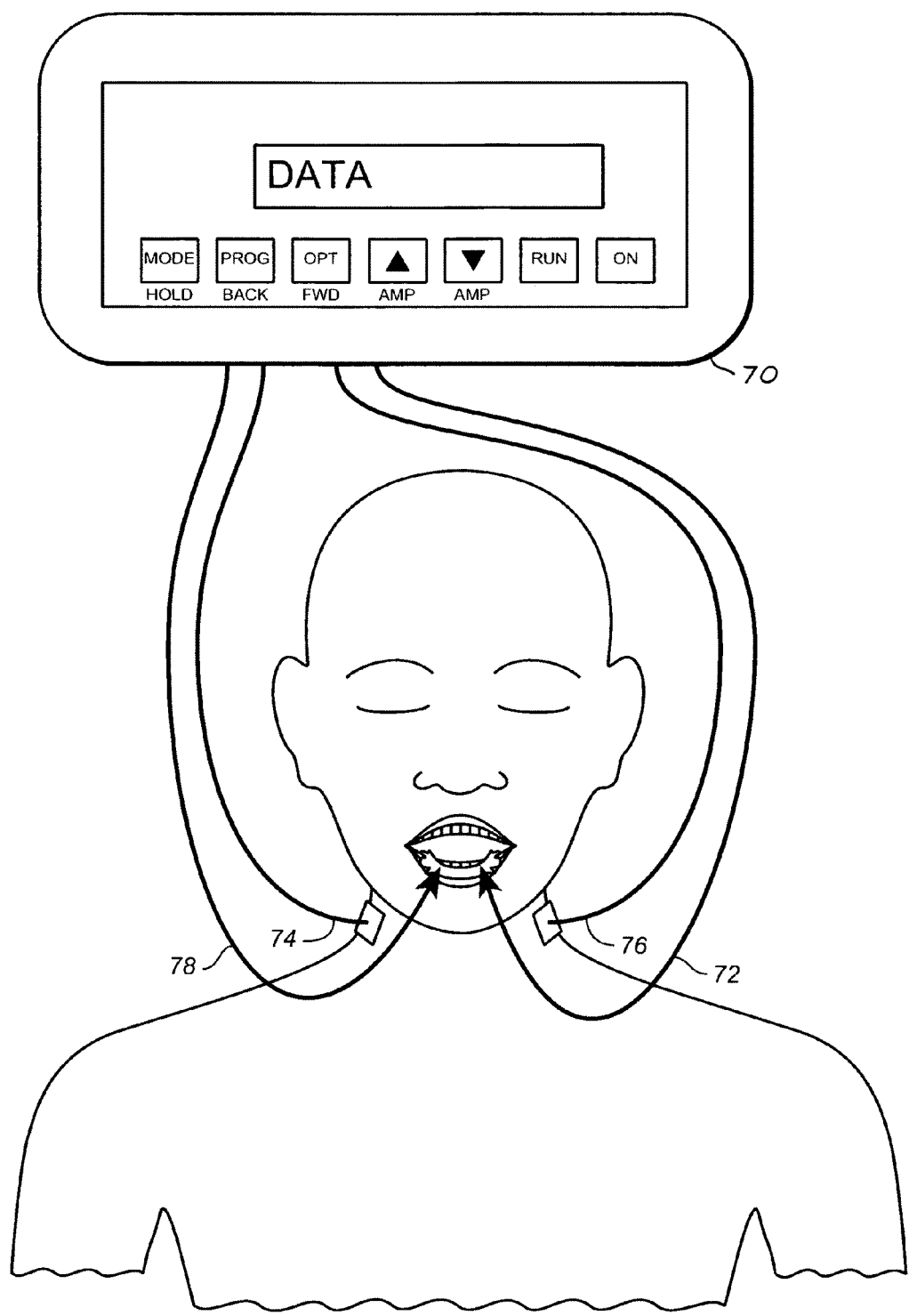
FIG. 1 is a diagram of an electrical simulation device to produce frequency specific microcurrent protocols in accordance with the various embodiments of the present invention.

In accordance with one aspect of the present invention, addressing inflammation is recognized to be a key approach to prevent or treat dental problems and the related complications that can lead to dental disease. Whereas periodontal disease is a local inflammatory disease initiated by bacteria characterized by neutrophil mediated tissue injury followed by development of a chronic immune lesion, "It is now becoming the mainstream understanding in dentistry that periodontal breakdown is not caused by oral bacteria, but by the body's own uncontrolled inflammatory response." Dr. Ken Southward, "Wellness Dentistry," September, 2006. Periodontal disease is not the only dental disease where inflammation is implicated as a causative factor. A whole new theory around the etiology of dental decay is also developing with inflammation at the crux. "With regard to dental caries, leading dental researchers are finding more evidence to support the theory of acid demineralization activating matrix metalloproteinase (MMP's) like collagenase. This results in carious breakdown of the dentin. What is new is the discovery that the host is the source of these MMP's. It is not the bacteria causing the damage after all. Dental decay is an uncontrolled inflammatory autoimmune breakdown just like periodontal disease." Dr. Ken Southward, "Wellness Dentistry," September, 2006.

According to the principles of the present invention, it is important to remember that inflammation is the body's response to trauma and infection. However, inflammation must be removed judiciously. In the mouth, the area to be treated must be examined for infection. If an active infection is present in the mouth, removing the inflammation without treating the infection can allow the infection to run rampant.

While addressing inflammation encountered in dentistry by applying frequency specific microcurrent is one of the underlying principles of the present invention, there are other underlying principles that relate to the particular frequency specific microcurrent protocols that are used. In accordance with another aspect of the present invention, as frequency specific microcurrent protocols related to dentistry were developed, not only the disease being prevented or treated, but the anatomy of the tissues in the affected region and the cellular process that was being affected were considered. Accordingly, understanding the anatomy of the mouth, the tooth, and the dental supporting structures is also recognized to be key.

Referring to Plate 61 in Frank H. Netter, M.D., *Atlas of Human Anatomy*, 4th Edition (2006), it is noted when observing the anatomy of the mouth, including the teeth and dental supporting structures, that a large variety of tissue types is present in a small region. In accordance with one aspect of the present invention, this wide variety of tissue types is a factor in determining the durations of the frequency specific microcurrent protocols, particularly in conjunction with oral surgery, as all of the types of affected tissue are preferably treated in conjunction with the surgery.

Considered in more detail, referring now to Plate 57 in Frank H. Netter, M.D., *Atlas of Human Anatomy*, 4th Edition (2006), a tooth has a hard crystalline outer covering called the enamel, an intermediate section called dentin, and an internal section called the pulp. The tooth is attached to the bone by an organ called the periodontal ligament. If the anatomy of the dentin is observed on an electron microscope, it is comprised of what are called dentinal tubules configured like a box of straws. The nerve in the pulp actually sends out demyelinated nerve fibers into these tubules which then carry stimuli back through the nerve to the brain. It is the nerve fibers in the tubules that are responsible for sensing pain and pressure. When the nerve in the pulp dies, these tubules become open and susceptible to bacteria and bacterial toxins.

During a root canal procedure, no matter how expertly the central nerve chamber is cleaned and debrided, it is virtually impossible to eliminate all the bacteria and their toxins in these tubules. The majority of root canal patients has an immune system that can successfully combat the residual bacteria that result from a root canal. On the other hand, patients with a compromised immune system or other medical problem, such as a blood clotting disorder, have difficulty eradicating the bacteria and fully healing. It is the dentinal anatomy that is one cause of osteitis resulting from root canal therapy.

In accordance with another aspect of the present invention, the anatomy and histology of the supporting structures of a tooth and their cellular function are factors in determining the frequencies of frequency specific microcurrent protocols. The periodontium is composed of four supporting structures for the teeth:

Gingiva: The gingiva forms a collar around the tooth, 1-9 mm wide, that is attached in part to the tooth and in part to the alveolar process.

Periodontal ligament: The thin ligament that attaches the cementum layer to the adjacent alveolar bone.

Cementum: The mineralized tissue covering the root dentin that serves to anchor periodontal ligament fibers.

Alveolar bone: The portion of the jawbone that houses the alveoli and the roots of the teeth.

Max A. Listgarten, D.D.S., Histology of the Periodontium University of Pennsylvania and Temple University (1999), http://www.dental.pitt.edu/informatics/periohistology/en/gu0102.htm, shows the anatomy of the periodontal structures in greater detail. Note the location of the periodontal ligament. In general, the periodontal ligament performs various functions that are essential for the long-term health of the dentin. Its primary function is supportive in attaching the tooth to the bone. In this function it serves as a shock absorber for chewing forces. The periodontal ligament also has a sensory function. The nerves come through the bone and branch to supply the nerve of the tooth and the periodontal ligament. The vascular cells in the periodontal ligament provide the nutrition that maintains the vitality of the tooth. This ligament is critically important in addressing dental pathology. Consequently, the histology and the function of the periodontal ligament need to be considered when developing frequency specific microcurrent protocols.

The periodontal ligament contains a unique assortment of cells that are capable of generating and maintaining three distinct tissues, namely, the ligament itself as well as the mineralized tissues on either side (i.e., the cementum and the alveolar bone). There are connective tissue cells, cells that are responsible for bone breakdown and deposition, cells that are responsible for tooth breakdown, as well as vascular and neural cells. The major cell types of the periodontal ligament include the following:

Fibroblasts, macrophages, and undifferentiated ectomesenchymal cells;

Cementoblasts and cementoclasts;

Osteoblasts and osteoclasts; and

Vascular and neural elements.

Considered in more detail, as shown in Max A. Listgarten, D.D.S., *Histology of the Periodontium*, University of Pennsylvania and Temple University (1999), http://www.dental.pitt.edu/informatics/periohistology/en/gu0401.htm, despite its fibrous nature, the periodontal ligament is a highly cellular structure that is able to perform a number of important functions that are essential for the long-term health of the masticatory structure. The periodontal ligament serves primarily a supportive function by attaching the tooth to the surrounding alveolar bone proper. This function is mediated primarily by the principal fibers of the periodontal ligament that form a strong fibrous union between the root cementum and the bone. The periodontal ligament also provides a cushioning mechanism in response to light as well as heavy forces. Light forces are cushioned by intravascular fluid that is forced out of the blood vessels. Moderate forces are absorbed by extravascular tissue fluid that is forced out of the periodontal ligament space into the adjacent marrow spaces. The heavier forces are handled by the principal fibers.

The periodontal ligament also serves a major remodeling function by providing cells that are able to form as well as resorb all the tissues that constitute the attachment structure, i.e., bone, cementum, and the periodontal ligament itself Undifferentiated ectomesenchymal cells, located around blood vessels, can differentiate into the specialized cells that form bone (osteoblasts), cementum (cementoblasts), and connective tissue fibers (fibroblasts). Bone- and tooth-resorbing cells (osteoclasts and odontoclasts) are generally multinucleated cells derived from blood-borne macrophages. The major remodeling function provided by the periodontal ligament is of particular interest when developing frequency specific microcurrent protocols in accordance with the various embodiments of the present invention.

The periodontal ligament also serves a sensory function. The myelinated nerves that perforate the fundus of the alveoli rapidly lose their myelinated sheath as they branch to supply both the pulp and periodontal ligament. The periodontal ligament is richly supplied with nerve endings that are primarily receptors for pain and pressure.

Finally, the periodontal ligament provides a nutritive function that maintains the vitality of its various cells. This ligament is well-vascularized, with the major blood supply originating from the dental arteries that enter the ligament through the fundus of the alveoli. Major anastomoses exist between blood vessels in the adjacent marrow spaces and the gingiva.

As shown in Max A. Listgarten, D.D.S., *Histology of the Periodontium*, University of Pennsylvania and Temple University (1999), http://www.dental.pitt.edu/informatics/periohistology/en/gu0602.htm, alveolar bone is produced by osteoblasts (OB) that are found in the periosteum, endosteum, and periodontal ligament. These specialized cells, called ectomesenchymal cells, originate from less differentiated precursor cells close to the bone. During bone formation, osteoblasts become incorporated into bone as osteocytes (OC) that are completely surrounded by bone. The chamber in which they are trapped is called a lacun. Osteocytes remain connected to osteoblasts and other osteocytes by cytoplasmic processes that run through small canals in the bone, which are called canaliculi (C). When developing frequency specific microcurrent protocols for periodontal disease and orthodontics, it is important to remember the origin of these cells as they serve such a vital role in wound healing and orthodontic tooth movement.

Despite its solid appearance, bone is in a constant state of remodeling. This means that at all times some parts of the jaw bone are being resorbed, while other parts are growing by apposition of new bone. This process requires some coordination between resorption and apposition so that the normal function of the bone can be maintained. Remodeling of the alveolar process allows for the normal migration of teeth in a mesial direction, orthodontic tooth movement, and wound healing following tooth removal and osseous surgery.

The frequency specific microcurrent protocols in accordance with the various embodiments of the present invention employ an electrical simulation device 70, as shown in FIG. 1. Preferably, the electrical stimulation device is a programmable source of variable frequency, variable amplitude electrical signals, whereby the frequency is capable of being varied within a range of approximately 0.1 to 970 hertz and the amplitude is capable of being varied within a range of approximately 20 to 400 microamps. The electrical simulation device has a plurality of electrodes capable of being connected to a patient, whereby the variable frequency and variable amplitude electrical signals are applied as electrical stimuli to a region proximate to the mouth of a patient to perform a predetermined protocol. This program feature allows for specific tissue and condition considerations. For example, the electrical stimulation device may be a commercially available CustomCare™ Patient Unit distributed by Precision Distributing located in Vancouver, Wash.

To create a customized mode for the CustomCare™ Patient Unit using an application programming interface, one can left click on an "Add User Mode" icon. A cursor will appear at the end of the list of modes with the next number in the sequence, the mode name line will be blank, and "User Mode" will appear in the right column identifier. One clicks in the "Mode Name Box" to name the new program (16 characters). One then programs the mode by clicking on the "Add Program" button. In the example of the CustomCare™ Patient Unit, a mode is programmed with the desired waveslope, frequencies, current, and polarity in sequence, as will now be described.

The electrical stimulation device preferably enables the waveslope to be programmed. In the example of the CustomCare™ Patient Unit, clicking a "Waveslope" box will bring down a pull down menu of waveslopes available. One can click on "Gentle," "Mild," "Sharp," or "Pulse" and that waveslope will be entered into a waveslope column. The "Gentle" waveslope is preferably selected for new injuries or trauma. The "Sharp" waveslope is preferably selected for chronic conditions.

The electrical stimulation device also enables the frequency to be programmed. Preferably, there are two pairs of electrodes to enable two frequencies to be selected. Accordingly, in the example of the CustomCare™ Patient Unit, one can enter a first frequency ("Freq1"). This is the Channel A frequency that is the first part of an A/B pair or the Condition frequency of a Condition/Tissue combination. One enters the number ending with the decimal point; if the number includes a decimal digit, one enters the decimal number after typing in the decimal point. The first selected frequency appears in the "Freq1" column.

In the example of the CustomCare™ Patient Unit, one can also enter a second frequency ("Freq2"). This is the Channel B frequency that is the second part of an A/B pair or the Tissue Type specific frequency of a Condition/Tissue combination. One enters the number ending with the decimal point; if the number includes a decimal digit, one enters the decimal number after typing in the decimal point. The second selected frequency appears in the "Freq2" column. Again, this program feature allows for the application of specific tissue and condition considerations.

The electrical stimulation device also enables the current level to be programmed. Accordingly, in the example of the CustomCare™ Patient Unit, one moves the cursor to a "Current" box. A drop down menu appears when the cursor moves into the box in the current column starting with 20 microamps and going up to 670 microamps. Typing the number 1 will bring the 100 microamp setting into the box automatically. One can enter a number into the box or move the cursor to one of the listed current levels and click on it. Typical applications use 100 microamps. Very ill patients may tolerate only 20 microamps. Athletes and even recreational body builders may tolerate 150 to 200 up to 400 microamps, for example. Only one of the listed current levels would be selected. The selected current appears in the "Current" column.

The electrical stimulation device also enables the duration to be programmed. In the example of the CustomCare™ Patient Unit, one moves the cursor into the "Duration" box and enters the number of minutes the frequency combination is to run.

The electrical stimulation device also enables the polarity to be programmed. In the example of the CustomCare™ Patient Unit, one moves the cursor to the "Polarity" box, which causes a drop down menu to appear with positive, negative, and alternating as choices. The use of positive polarity is preferably selected in the case of an acute condition involving the nerves. One clicks on the desired polarity or enters the first letter such as "a" to select an alternating polarity setting, or "p" to select a positive polarity setting.

As described above, two pairs of electrodes are preferably provided. In the example of the CustomCare™ Patient Unit, the leads are color coordinated. The leads are typically attached to a patient's head and neck with adhesive conductive pads. As shown in FIG. 1, a Black lead 72 is connected across from a Red lead 74, and a Yellow lead 78 is connected across from a Green lead 76. That is, the adhesive electrode pads or connections are arranged so that the Black and Yellow leads 72 and 78 are on one side of the region to be treated, and the Red and Green leads 74 and 76 are on the other side in three dimensions, and the Black and Red leads and Yellow and Green leads are across from each other.

Various frequency specific microcurrent protocols have been developed in accordance with the embodiments of the present invention for use when treating dental and orthodontic patients. The dental problems prevented or treated and the associated frequency specific microcurrent protocols are as follows.

In accordance with various embodiments of the present invention, frequency specific microcurrent protocols are provided for use in conjunction with the following dental and orthodontic procedures:
  Gingival Surgery and Chronic Periodontitis
  Implant/Osseous Periodontal Surgery
  General Post Operative Trauma
  Pulpal Trauma
  Pulpal Inflammation
  Root Canal Post Op.
  Chronic Osteonecrosis
  Osteonecrosis Surgery Post Op
  Orthodontic Protocol—Prevent Pain
  Orthodontic Protocol—Mid-Adjustment Considered in more detail, a frequency specific microcurrent protocol is provided in accordance with one embodiment of the present invention for use in conjunction with gingival surgery and chronic periodontitis. This protocol is used in association with gingival soft tissue surgery, scaling and root planing, and other periodontal procedures to prevent pain and swelling and to speed healing. Preferably, the Red and Green leads 74 and 76 with adhesive pads are placed on the back of the patient's neck, and the Black and Yellow leads 72 and 78 may be attached by alligator clips to wet 4×4 gauze in the patient's mouth (with the Red lead opposite the Black lead and the Green lead opposite the Yellow lead). The preferred parameters for the gingival surgery and chronic periodontitis protocol have the following approximate values.

| Mode Code: 0086 | | | T-Ging Surgery | | | Type: User | |
|---|---|---|---|---|---|---|---|
| Seq | Waveshape | Freq1 | Freq2 | Current | Duration | Polarity | Mode |
| 0.9 | Gentle | 18.0 | 62.0 | 100 | 3 | Alternating | Auto |
| 1.1 | Gentle | 18.0 | 142.0 | 100 | 3 | Alternating | Auto |
| 1.2 | Gentle | 18.0 | 396.0 | 100 | 3 | Alternating | Auto |
| 1.8 | Gentle | 18.0 | 70.0 | 100 | 3 | Alternating | Auto |
| 1.9 | Gentle | 19.0 | 124.0 | 100 | 2 | Alternating | Auto |
| 2.0 | Gentle | 19.0 | 45.0 | 100 | 2 | Alternating | Auto |
| 2.1 | Gentle | 19.0 | 142.0 | 100 | 2 | Alternating | Auto |
| 3.0 | Gentle | 124.0 | 124.0 | 100 | 1 | Alternating | Auto |
| 3.1 | Gentle | 124.0 | 62.0 | 100 | 1 | Alternating | Auto |
| 4.0 | Gentle | 124.0 | 142.0 | 100 | 1 | Alternating | Auto |
| 4.1 | Gentle | 124.0 | 70.0 | 100 | 1 | Alternating | Auto |
| 5.0 | Gentle | 124.0 | 77.0 | 100 | 1 | Alternating | Auto |
| 5.1 | Gentle | 124.0 | 783.0 | 100 | 1 | Alternating | Auto |
| 6.0 | Gentle | 294.0 | 62.0 | 100 | 1 | Alternating | Auto |
| 7.0 | Gentle | 294.0 | 142.0 | 100 | 1 | Alternating | Auto |
| 7.1 | Gentle | 294.0 | 70.0 | 100 | 1 | Alternating | Auto |
| 8.0 | Gentle | 294.0 | 77.0 | 100 | 1 | Alternating | Auto |
| 8.1 | Gentle | 294.0 | 783.0 | 100 | 1 | Alternating | Auto |
| 9.0 | Gentle | 321.0 | 62.0 | 100 | 1 | Alternating | Auto |
| 10.0 | Gentle | 321.0 | 142.0 | 100 | 1 | Alternating | Auto |
| 10.1 | Gentle | 321.0 | 70.0 | 100 | 1 | Alternating | Auto |
| 11.0 | Gentle | 321.0 | 77.0 | 100 | 1 | Alternating | Auto |

-continued

| | Mode Code: 0086 | | T-Ging Surgery | | Type: User | |
|---|---|---|---|---|---|---|
| Seq | Waveshape | Freq1 | Freq2 | Current | Duration | Polarity Mode |
| 11.1 | Gentle | 321.0 | 783.0 | 100 | 1 | Alternating Auto |
| 12.0 | Gentle | 9.0 | 62.0 | 100 | 1 | Alternating Auto |
| 13.0 | Gentle | 9.0 | 142.0 | 100 | 1 | Alternating Auto |
| 13.1 | Gentle | 9.0 | 70.0 | 100 | 1 | Alternating Auto |
| 14.0 | Gentle | 9.0 | 77.0 | 100 | 1 | Alternating Auto |
| 14.1 | Gentle | 9.0 | 783.0 | 100 | 1 | Alternating Auto |
| 15.0 | Gentle | 40.0 | 116.0 | 100 | 4 | Alternating Auto |
| 16.0 | Gentle | 40.0 | 142.0 | 100 | 4 | Alternating Auto |
| 17.0 | Gentle | 40.0 | 62.0 | 100 | 4 | Alternating Auto |
| 17.1 | Gentle | 40.0 | 77.0 | 100 | 4 | Alternating Auto |
| 17.1 | Gentle | 40.0 | 70.0 | 100 | 4 | Alternating Auto |
| 17.2 | Gentle | 40.0 | 783.0 | 100 | 4 | Alternating Auto |
| 18.0 | Gentle | 81.0 | 142.0 | 100 | 3 | Alternating Auto |
| 18.2 | Gentle | 81.0 | 77.0 | 100 | 3 | Alternating Auto |
| 18.3 | Gentle | 81.0 | 70.0 | 100 | 3 | Alternating Auto |
| 19.0 | Gentle | 49.0 | 62.0 | 100 | 1 | Alternating Auto |
| 20.0 | Gentle | 49.0 | 142.0 | 100 | 1 | Alternating Auto |
| 21.0 | Gentle | 49.0 | 77.0 | 100 | 1 | Alternating Auto |
| 22.0 | Gentle | 49.0 | 70.0 | 100 | 1 | Alternating Auto |

Figure 2:
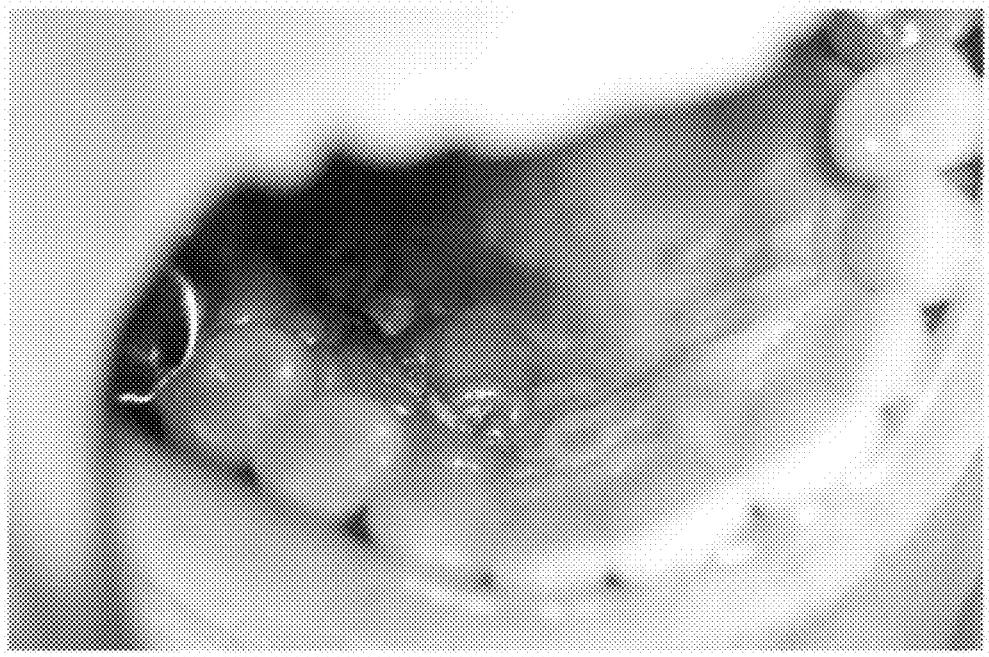
FIG. 2 shows patient results after gingival grafting when the gingival surgery and chronic periodontitis protocol in accordance with one embodiment of the present invention was used in conjunction with gingival surgery.
Figure 3:
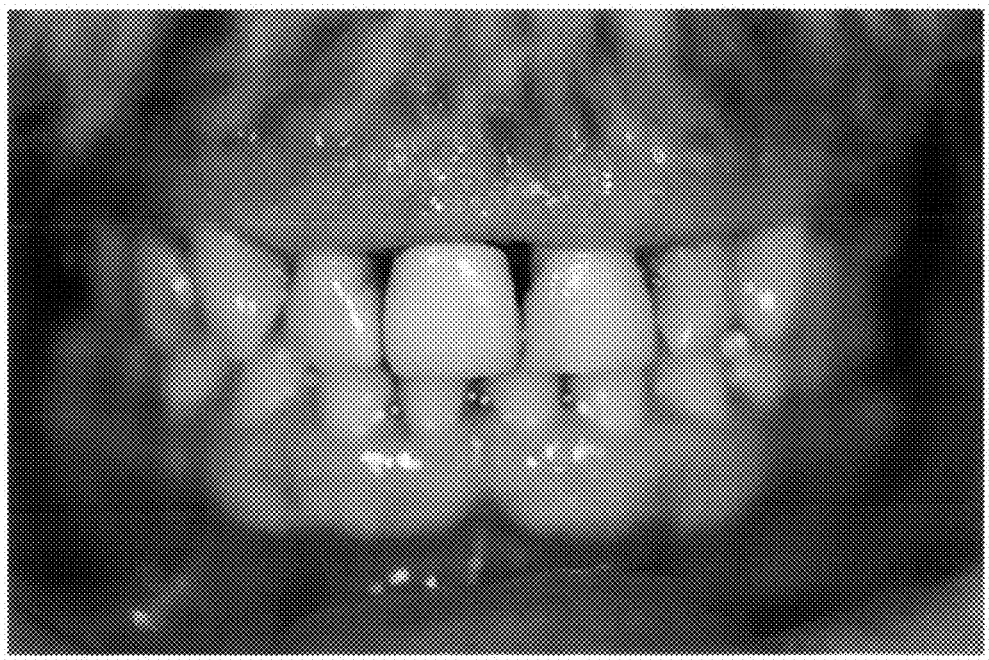
FIG. 3 shows patient results after four quadrants of scaling and root planing when the gingival surgery and chronic periodontitis protocol in accordance with one embodiment of the present invention was used in conjunction with the scaling and root planing procedure.

FIG. 2 shows the results for Melanie C. 24 hours after gingival grafting performed in conjunction with using the gingival surgery and chronic periodontitis protocol. She experienced no pain in the palatal donor site. FIG. 3 shows the results for Bill F. one week after four quadrants of scaling and root planing performed in conjunction with using the gingival surgery and chronic periodontitis protocol.

A frequency specific microcurrent protocol is also provided in accordance with one embodiment of the present invention for use in conjunction with implant/osseous surgery. This protocol is similar to the gingival soft tissue protocol, but the frequencies for bone are added. Preferably, the Red and Green leads 74 and 76 with adhesive pads are placed on the back of the patient's neck, and the Black and Yellow leads 72 and 78 may be attached by alligator clips to wet 4×4 gauze in the patient's mouth (with the Red lead opposite the Black lead and the Green lead opposite the Yellow lead). The preferred parameters for the implant/osseous surgery protocol have the following approximate values.

| | Mode Code: 0094 | | T-Implant Surg | | Type: User | |
|---|---|---|---|---|---|---|
| Seq | Waveshape | Freq1 | Freq2 | Current | Duration | Polarity Mode |
| 0.9 | Gentle | 18.0 | 124.0 | 100 | 3 | Alternating Auto |
| 1.1 | Gentle | 18.0 | 142.0 | 100 | 3 | Alternating Auto |
| 1.2 | Gentle | 18.0 | 396.0 | 100 | 3 | Alternating Auto |
| 1.8 | Gentle | 18.0 | 70.0 | 100 | 3 | Alternating Auto |
| 1.9 | Gentle | 19.0 | 124.0 | 100 | 2 | Alternating Auto |
| 2.0 | Gentle | 19.0 | 45.0 | 100 | 2 | Alternating Auto |
| 2.1 | Gentle | 19.0 | 142.0 | 100 | 2 | Alternating Auto |
| 3.0 | Gentle | 124.0 | 124.0 | 100 | 1 | Alternating Auto |
| 3.1 | Gentle | 124.0 | 62.0 | 100 | 1 | Alternating Auto |
| 4.0 | Gentle | 124.0 | 142.0 | 100 | 1 | Alternating Auto |
| 4.1 | Gentle | 124.0 | 70.0 | 100 | 1 | Alternating Auto |
| 5.0 | Gentle | 124.0 | 77.0 | 100 | 1 | Alternating Auto |
| 5.1 | Gentle | 124.0 | 783.0 | 100 | 2 | Alternating Auto |
| 5.2 | Gentle | 124.0 | 59.0 | 100 | 2 | Alternating Auto |
| 5.3 | Gentle | 124.0 | 39.0 | 100 | 2 | Alternating Auto |
| 6.0 | Gentle | 294.0 | 62.0 | 100 | 1 | Alternating Auto |
| 7.0 | Gentle | 294.0 | 142.0 | 100 | 1 | Alternating Auto |
| 7.1 | Gentle | 294.0 | 70.0 | 100 | 1 | Alternating Auto |
| 8.0 | Gentle | 294.0 | 77.0 | 100 | 1 | Alternating Auto |
| 8.1 | Gentle | 294.0 | 783.0 | 100 | 1 | Alternating Auto |
| 9.0 | Gentle | 321.0 | 62.0 | 100 | 1 | Alternating Auto |
| 10.0 | Gentle | 321.0 | 142.0 | 100 | 1 | Alternating Auto |
| 10.1 | Gentle | 321.0 | 70.0 | 100 | 1 | Alternating Auto |
| 11.0 | Gentle | 321.0 | 77.0 | 100 | 1 | Alternating Auto |

-continued

| | Mode Code: 0094 | | T-Implant Surg | | Type: User | |
|---|---|---|---|---|---|---|
| Seq | Waveshape | Freq1 | Freq2 | Current | Duration | Polarity Mode |
| 11.1 | Gentle | 321.0 | 783.0 | 100 | 1 | Alternating Auto |
| 12.0 | Gentle | 9.0 | 62.0 | 100 | 1 | Alternating Auto |
| 13.0 | Gentle | 9.0 | 142.0 | 100 | 1 | Alternating Auto |
| 13.1 | Gentle | 9.0 | 70.0 | 100 | 1 | Alternating Auto |
| 14.0 | Gentle | 9.0 | 77.0 | 100 | 1 | Alternating Auto |
| 14.1 | Gentle | 9.0 | 783.0 | 100 | 1 | Alternating Auto |
| 15.0 | Gentle | 40.0 | 116.0 | 100 | 4 | Alternating Auto |
| 16.0 | Gentle | 40.0 | 142.0 | 100 | 4 | Alternating Auto |
| 17.0 | Gentle | 40.0 | 62.0 | 100 | 4 | Alternating Auto |
| 17.1 | Gentle | 40.0 | 77.0 | 100 | 4 | Alternating Auto |
| 17.1 | Gentle | 40.0 | 70.0 | 100 | 4 | Alternating Auto |
| 17.2 | Gentle | 40.0 | 783.0 | 100 | 4 | Alternating Auto |
| 17.3 | Gentle | 40.0 | 59.0 | 100 | 4 | Alternating Auto |
| 17.4 | Gentle | 40.0 | 39.0 | 100 | 4 | Alternating Auto |
| 18.0 | Gentle | 81.0 | 142.0 | 100 | 3 | Alternating Auto |
| 18.2 | Gentle | 81.0 | 77.0 | 100 | 3 | Alternating Auto |
| 18.3 | Gentle | 81.0 | 70.0 | 100 | 3 | Alternating Auto |
| 19.0 | Gentle | 49.0 | 62.0 | 100 | 1 | Alternating Auto |
| 20.0 | Gentle | 49.0 | 142.0 | 100 | 1 | Alternating Auto |
| 21.0 | Gentle | 49.0 | 77.0 | 100 | 1 | Alternating Auto |
| 22.0 | Gentle | 49.0 | 70.0 | 100 | 1 | Alternating Auto |
| 23.0 | Gentle | 49.0 | 59.0 | 100 | 1 | Alternating Auto |
| 24.0 | Gentle | 49.0 | 39.0 | 100 | 1 | Alternating Auto |
| 25.0 | Gentle | 81.0 | 783.0 | 100 | 3 | Alternating Auto |
| 26.0 | Gentle | 49.0 | 39.0 | 100 | 1 | Alternating Auto |

Figure 4:
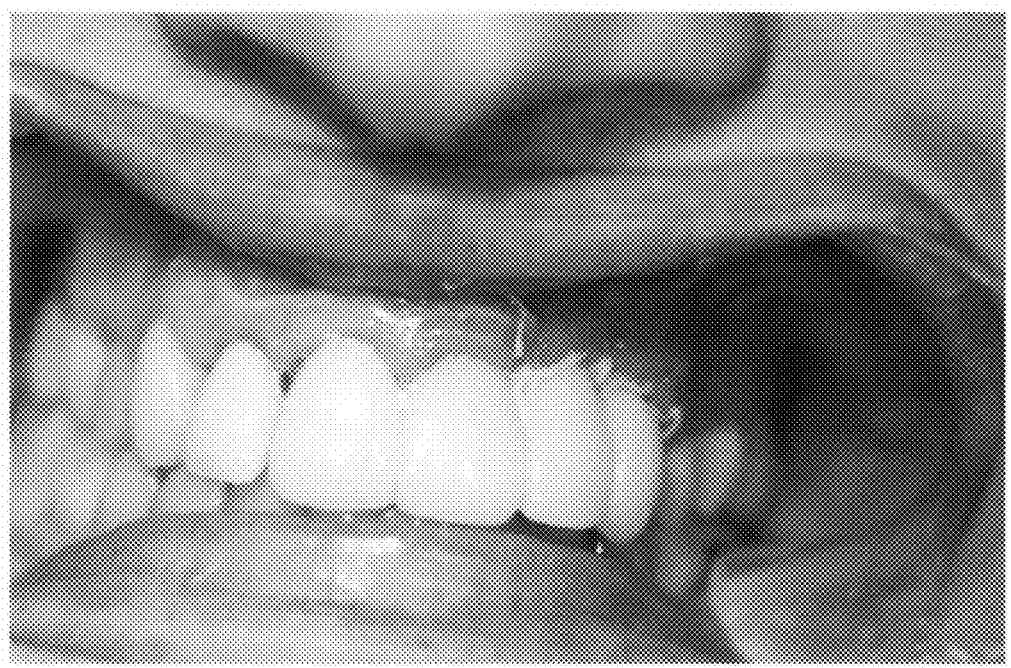
FIG. 4 shows patient results when the implant/osseous surgery protocol in accordance with one embodiment of the present invention was used in conjunction with implant surgery.

FIG. 4 shows the results of implant surgery for Robin L. performed in conjunction with using the implant/osseous surgery protocol. These results are three days post op.

A frequency specific microcurrent protocol is additionally provided in accordance with one embodiment of the present invention for use in conjunction with general post operative trauma. This protocol is used after a dental visit to prevent pain and soreness after treatment affecting the jaw, gums, and teeth. Preferably, the Red and Green leads 74 and 76 with adhesive pads are placed on the back of the patient's neck. Alternatively, the adhesive pads can be placed on the cheeks of the patient. The Black and Yellow leads 72 and 78 may be attached by alligator clips to wet 4×4 gauze in the patient's mouth (with the Red lead opposite the Black lead and the Green lead opposite the Yellow lead). The preferred parameters for the general post operative trauma protocol have the following approximate values.

| | Mode Code: 0088 | | T-Post Op | | Type: User | |
|---|---|---|---|---|---|---|
| Seq | Waveshape | Freq1 | Freq2 | Current | Duration | Polarity Mode |
| 1.0 | Sharp | 94.0 | 200.0 | 100 | 1 | Alternating Auto |
| 2.0 | Sharp | 970.0 | 13.0 | 100 | 1 | Alternating Auto |
| 3.0 | Sharp | 970.0 | 200.0 | 100 | 1 | Alternating Auto |
| 4.0 | Sharp | 94.0 | 94.0 | 100 | 1 | Alternating Auto |
| 5.0 | Sharp | 6.8 | 38.0 | 100 | 1 | Alternating Auto |
| 6.0 | Sharp | 60.0 | 0.1 | 100 | 1 | Alternating Auto |
| 7.0 | Sharp | 66.0 | 0.1 | 100 | 1 | Alternating Auto |
| 8.0 | Sharp | 64.0 | 42.0 | 100 | 1 | Alternating Auto |
| 9.0 | Sharp | 64.0 | 63.0 | 100 | 1 | Alternating Auto |
| 10.0 | Gentle | 18.0 | 62.0 | 100 | 3 | Alternating Auto |
| 11.0 | Gentle | 18.0 | 142.0 | 100 | 2 | Alternating Auto |
| 12.0 | Gentle | 18.0 | 396.0 | 100 | 2 | Alternating Auto |
| 13.0 | Gentle | 19.0 | 45.0 | 100 | 2 | Alternating Auto |
| 14.0 | Gentle | 19.0 | 142.0 | 100 | 2 | Alternating Auto |
| 15.0 | Gentle | 124.0 | 62.0 | 100 | 1 | Alternating Auto |
| 16.0 | Gentle | 124.0 | 142.0 | 100 | 1 | Alternating Auto |
| 17.0 | Gentle | 124.0 | 191.0 | 100 | 1 | Alternating Auto |
| 18.0 | Gentle | 124.0 | 783.0 | 100 | 1 | Alternating Auto |
| 19.0 | Gentle | 124.0 | 243.0 | 100 | 1 | Alternating Auto |
| 20.0 | Gentle | 40.0 | 62.0 | 100 | 2 | Alternating Auto |
| 21.0 | Gentle | 40.0 | 142.0 | 100 | 2 | Alternating Auto |

-continued

| Mode Code: 0088 | | T-Post Op | | Type: User | | |
|---|---|---|---|---|---|---|
| Seq | Waveshape | Freq1 | Freq2 | Current | Duration | Polarity | Mode |
| 22.0 | Gentle | 40.0 | 191.0 | 100 | 2 | Alternating | Auto |
| 23.0 | Gentle | 40.0 | 783.0 | 100 | 2 | Alternating | Auto |
| 24.0 | Gentle | 40.0 | 243.0 | 100 | 2 | Alternating | Auto |
| 24.1 | Gentle | 40.0 | 41.0 | 100 | 2 | Alternating | Auto |
| 25.0 | Gentle | 94.0 | 396.0 | 100 | 1 | Alternating | Auto |
| 26.0 | Gentle | 40.0 | 396.0 | 100 | 1 | Alternating | Auto |
| 27.0 | Gentle | 294.0 | 41.0 | 100 | 1 | Alternating | Auto |
| 28.0 | Gentle | 321.0 | 41.0 | 100 | 1 | Alternating | Auto |
| 29.0 | Gentle | 9.0 | 41.0 | 100 | 1 | Alternating | Auto |
| 30.0 | Gentle | 294.0 | 62.0 | 100 | 1 | Alternating | Auto |
| 31.0 | Gentle | 321.0 | 62.0 | 100 | 1 | Alternating | Auto |
| 32.0 | Gentle | 9.0 | 62.0 | 100 | 1 | Alternating | Auto |
| 33.0 | Gentle | 49.0 | 62.0 | 100 | 1 | Alternating | Auto |
| 34.0 | Gentle | 81.0 | 142.0 | 100 | 2 | Alternating | Auto |
| 35.0 | Gentle | 49.0 | 142.0 | 100 | 1 | Alternating | Auto |

Prior to the introduction of pulpal trauma and pulpal inflammation protocols, the background and current standard of care for the treatment of the tooth nerve will be described. Tooth nerve pain may be due to a pulpitis, which can either be acute or chronic and reversible or irreversible, as diagnosed by the treating dentist. Infection or abscess may or may not be present. In the current treatment of root canals, there is no differentiation in the course of treatment between an inflamed pulp and an infected abscessed pulp. The present invention provides an alternative to current root canal therapy in the treatment of vital pulpitis.

Accordingly, a frequency specific microcurrent protocol is provided in accordance with one embodiment of the present invention for use in conjunction with pulpal trauma. This protocol is used when a patient is having tooth pain following dental treatment, oral trauma, or is diagnosed with acute or chronic inflammatory pulpitis. Preferably, the Red and Green leads 74 and 76 with adhesive pads are placed on the back of the patient's neck, and the Black and Yellow leads 72 and 76 may be attached by alligator clips to wet 4×4 gauze in the patient's mouth (with the Red lead opposite the Black lead and the Green lead opposite the Yellow lead). The preferred parameters for the pulpal trauma protocol have the following approximate values.

| Mode Code: 0093 | | Pulpal Trauma A | | Type: User | | |
|---|---|---|---|---|---|---|
| Seq | Waveshape | Freq1 | Freq2 | Current | Duration | Polarity | Mode |
| 1.0 | Gentle | 94.0 | 200.0 | 100 | 1 | Alternating | Auto |
| 2.0 | Gentle | 94.0 | 94.0 | 100 | 1 | Alternating | Auto |
| 3.0 | Gentle | 94.0 | 45.0 | 100 | 1 | Alternating | Auto |
| 4.0 | Gentle | 970.0 | 200.0 | 100 | 1 | Alternating | Auto |
| 5.0 | Gentle | 6.8 | 38.0 | 100 | 1 | Alternating | Auto |
| 6.0 | Gentle | 60.0 | 0.1 | 100 | 1 | Alternating | Auto |
| 7.0 | Gentle | 66.0 | 0.1 | 100 | 1 | Alternating | Auto |
| 8.0 | Gentle | 64.0 | 42.0 | 100 | 1 | Alternating | Auto |
| 9.0 | Gentle | 64.0 | 63.0 | 100 | 1 | Alternating | Auto |
| 10.0 | Gentle | 97.0 | 40.0 | 100 | 1 | Alternating | Auto |
| 11.0 | Gentle | 98.0 | 20.0 | 100 | 1 | Alternating | Auto |
| 12.0 | Gentle | 18.0 | 62.0 | 100 | 3 | Alternating | Auto |
| 13.0 | Gentle | 19.0 | 45.0 | 100 | 2 | Alternating | Auto |
| 14.0 | Gentle | 124.0 | 396.0 | 100 | 1 | Alternating | Auto |
| 15.0 | Gentle | 124.0 | 62.0 | 100 | 1 | Alternating | Auto |
| 16.0 | Gentle | 124.0 | 41.0 | 100 | 1 | Alternating | Auto |
| 17.0 | Gentle | 124.0 | 77.0 | 100 | 1 | Alternating | Auto |
| 18.0 | Gentle | 124.0 | 100.0 | 100 | 1 | Alternating | Auto |
| 19.0 | Gentle | 294.0 | 396.0 | 100 | 1 | Alternating | Auto |
| 20.0 | Gentle | 294.0 | 62.0 | 100 | 1 | Alternating | Auto |
| 21.0 | Gentle | 294.0 | 41.0 | 100 | 1 | Alternating | Auto |
| 22.0 | Gentle | 294.0 | 77.0 | 100 | 1 | Alternating | Auto |
| 23.0 | Gentle | 294.0 | 100.0 | 100 | 1 | Alternating | Auto |
| 24.0 | Gentle | 321.0 | 396.0 | 100 | 1 | Alternating | Auto |
| 25.0 | Gentle | 321.0 | 62.0 | 100 | 1 | Alternating | Auto |
| 26.0 | Gentle | 321.0 | 41.0 | 100 | 1 | Alternating | Auto |
| 27.0 | Gentle | 321.0 | 77.0 | 100 | 1 | Alternating | Auto |
| 28.0 | Gentle | 321.0 | 100.0 | 100 | 1 | Alternating | Auto |
| 29.0 | Gentle | 9.0 | 396.0 | 100 | 1 | Alternating | Auto |
| 30.0 | Gentle | 9.0 | 62.0 | 100 | 1 | Alternating | Auto |
| 31.0 | Gentle | 9.0 | 41.0 | 100 | 1 | Alternating | Auto |
| 32.0 | Gentle | 9.0 | 77.0 | 100 | 1 | Alternating | Auto |
| 33.0 | Gentle | 9.0 | 100.0 | 100 | 1 | Alternating | Auto |
| 34.0 | Gentle | 40.0 | 116.0 | 100 | 4 | Alternating | Auto |
| 35.0 | Gentle | 40.0 | 396.0 | 100 | 4 | Alternating | Auto |
| 36.0 | Gentle | 40.0 | 41.0 | 100 | 4 | Alternating | Auto |
| 37.0 | Gentle | 40.0 | 62.0 | 100 | 4 | Alternating | Auto |
| 38.0 | Gentle | 40.0 | 77.0 | 100 | 1 | Alternating | Auto |
| 39.0 | Gentle | 40.0 | 100.0 | 100 | 1 | Alternating | Auto |
| 40.0 | Gentle | 40.0 | 396.0 | 100 | 4 | Alternating | Auto |
| 41.0 | Gentle | 49.0 | 396.0 | 100 | 1 | Alternating | Auto |
| 42.0 | Gentle | 49.0 | 62.0 | 100 | 1 | Alternating | Auto |
| 43.0 | Gentle | 49.0 | 41.0 | 100 | 1 | Alternating | Auto |
| 44.0 | Gentle | 49.0 | 77.0 | 100 | 1 | Alternating | Auto |

Figure 5:
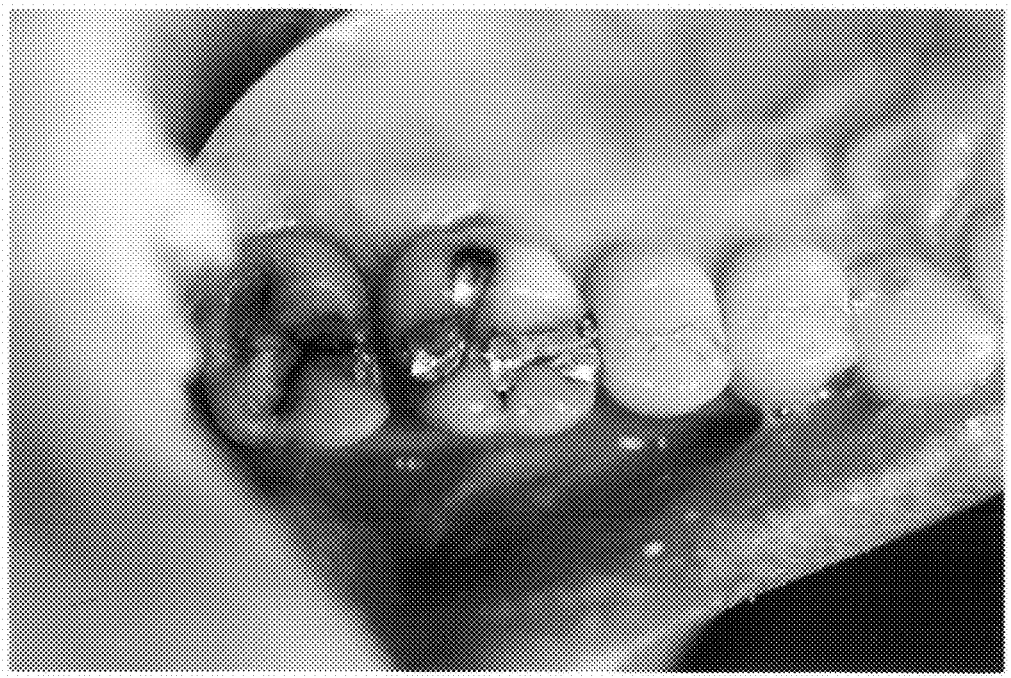
FIG. 5 shows results for a patient who experienced acute inflammatory pulpitis and was treated using a standard concussion protocol, as well as the pulpal trauma protocol in accordance with one embodiment of the present invention.

FIG. 5 shows the results for Dennis D. This patient experienced acute inflammatory pulpitis, subsequent to partially fracturing tooth #2. The tooth was prepared for a partial coverage gold crown and a temporary crown was placed on the tooth. A standard concussion protocol was administered, as well as the above-described pulpal trauma protocol. The patient was pain-free the day following treatment. A permanent crown was subsequently placed with a temporary cement. The tooth is currently asymptomatic and will be followed for maintenance of pulpal vitality.

In the case of the pulpal trauma protocol, the tooth to be treated must be examined for infection and pulpal vitality. The application of frequency specific microcurrent to a tooth diagnosed as non-vital and infected will not restore the tooth to health, and removal of the inflammation without treatment of the infection could make the situation worse. Advantageously, the frequencies used for the pulpal trauma protocol have been effective in treating nerve pulpitis in a vital tooth and have avoided immediate and subsequent root canal therapy.

Additionally, a frequency specific microcurrent protocol is provided in accordance with one embodiment of the present invention for use in conjunction with pulpal inflammation. This protocol is used to address pain and inflammation in the nerve when a tooth is diagnosed with acute inflammatory pulpitis. Preferably, this protocol is administered following the above-described pulpal trauma protocol if nerve pain persists. Preferably, the Red and Green leads 74 and 76 with adhesive pads are placed on the back of the patient's neck, and the Black and Yellow leads 72 and 78 may be attached by alligator clips to wet 4×4 gauze in the patient's mouth (with the Red lead opposite the Black lead and the Green lead opposite the Yellow lead). The preferred parameters for the pulpal inflammation protocol have the following approximate values.

| Mode Code: 0087 | | Pulpal Inflamm | | Type: User | | |
|---|---|---|---|---|---|---|
| Seq | Waveshape | Freq1 | Freq2 | Current | Duration | Polarity | Mode |
| 1.0 | Sharp | 94.0 | 200.0 | 100 | 1 | Alternating | Auto |
| 2.0 | Sharp | 970.0 | 200.0 | 100 | 1 | Alternating | Auto |
| 3.0 | Sharp | 6.8 | 38.0 | 100 | 1 | Alternating | Auto |

-continued

| Mode Code: 0087 | | Pulpal Inflamm | | | Type: User | |
|---|---|---|---|---|---|---|
| Seq | Waveshape | Freq1 | Freq2 | Current | Duration Polarity | Mode |
| 4.0 | Sharp | 60.0 | 0.1 | 100 | 1 Alternating | Auto |
| 5.0 | Sharp | 66.0 | 0.1 | 100 | 1 Alternating | Auto |
| 6.0 | Sharp | 64.0 | 42.0 | 100 | 1 Alternating | Auto |
| 7.0 | Sharp | 64.0 | 63.0 | 100 | 1 Alternating | Auto |
| 8.0 | Sharp | 97.0 | 40.0 | 100 | 1 Alternating | Auto |
| 9.0 | Sharp | 98.0 | 20.0 | 100 | 1 Alternating | Auto |
| 10.0 | Sharp | 40.0 | 396.0 | 100 | 20 Positive | Auto |
| 11.0 | Sharp | 284.0 | 396.0 | 100 | 5 Positive | Auto |
| 12.0 | Sharp | 18.0 | 396.0 | 100 | 2 Positive | Auto |
| 13.0 | Sharp | 94.0 | 396.0 | 100 | 1 Positive | Auto |
| 14.0 | Sharp | 124.0 | 396.0 | 100 | 1 Positive | Auto |
| 15.0 | Sharp | 321.0 | 396.0 | 100 | 1 Positive | Auto |
| 16.0 | Sharp | 9.0 | 396.0 | 100 | 1 Positive | Auto |
| 17.0 | Sharp | 3.0 | 396.0 | 100 | 2 Positive | Auto |
| 18.0 | Sharp | 13.0 | 396.0 | 100 | 2 Positive | Auto |
| 19.0 | Sharp | 91.0 | 396.0 | 100 | 2 Positive | Auto |
| 20.0 | Sharp | 40.0 | 62.0 | 100 | 4 Alternating | Auto |
| 21.0 | Sharp | 284.0 | 62.0 | 100 | 2 Alternating | Auto |
| 22.0 | Sharp | 124.0 | 62.0 | 100 | 1 Alternating | Auto |
| 23.0 | Sharp | 321.0 | 62.0 | 100 | 1 Alternating | Auto |
| 24.0 | Sharp | 9.0 | 62.0 | 100 | 1 Alternating | Auto |
| 25.0 | Sharp | 91.0 | 62.0 | 100 | 2 Alternating | Auto |
| 25.1 | Sharp | 50.0 | 13.0 | 100 | 1 Positive | Auto |
| 25.2 | Sharp | 81.0 | 13.0 | 100 | 1 Positive | Auto |
| 25.3 | Sharp | 50.0 | 13.0 | 100 | 1 Positive | Auto |
| 25.4 | Sharp | 81.0 | 13.0 | 100 | 1 Positive | Auto |
| 25.5 | Sharp | 50.0 | 13.0 | 100 | 1 Positive | Auto |
| 26.0 | Sharp | 81.0 | 396.0 | 100 | 2 Positive | Auto |
| 27.0 | Sharp | 49.0 | 396.0 | 100 | 1 Positive | Auto |

The clinician must ascertain that the pulp is vital and that there is no acute or chronic infection. Advantageously, the frequencies used for the pulpal inflammation protocol when used to treat vital pulpitis have been effective for avoiding root canal therapy.

Also, a frequency specific microcurrent protocol is provided in accordance with one embodiment of the present invention for use in conjunction with root canal post op care. Immediately following root canal therapy (RCT), this protocol prevents post operative pain and inflammation in the periodontal ligament. Preferably, the Red and Green leads 74 and 76 with adhesive pads are placed on the back of the patient's neck, and the Black and Yellow leads 72 and 78 may be attached by alligator clips to wet 4×4 gauze in the patient's mouth (with the Red lead opposite the Black lead and the Green lead opposite the Yellow lead). The preferred parameters for the root canal post op protocol have the following approximate values.

| Mode Code: 0089 | | RCT Post OP | | | Type: User | |
|---|---|---|---|---|---|---|
| Seq | Waveshape | Freq1 | Freq2 | Current | Duration Polarity | Mode |
| 1.0 | Sharp | 94.0 | 200.0 | 100 | 1 Alternating | Auto |
| 2.0 | Sharp | 970.0 | 200.0 | 100 | 1 Alternating | Auto |
| 3.0 | Sharp | 970.0 | 13.0 | 100 | 1 Alternating | Auto |
| 4.0 | Sharp | 94.0 | 94.0 | 100 | 1 Alternating | Auto |
| 5.0 | Sharp | 6.8 | 38.0 | 100 | 2 Alternating | Auto |
| 5.1 | Sharp | 60.0 | 0.1 | 100 | 1 Alternating | Auto |
| 5.2 | Sharp | 66.0 | 0.1 | 100 | 1 Alternating | Auto |
| 6.0 | Sharp | 64.0 | 42.0 | 100 | 1 Alternating | Auto |
| 7.0 | Sharp | 64.0 | 63.0 | 100 | 1 Alternating | Auto |
| 7.1 | Sharp | 460.0 | 650.0 | 100 | 1 Alternating | Auto |
| 7.2 | Sharp | 97.0 | 40.0 | 100 | 1 Alternating | Auto |
| 7.3 | Sharp | 98.0 | 20.0 | 100 | 1 Alternating | Auto |
| 7.4 | Sharp | 12.0 | 41.0 | 100 | 1 Alternating | Auto |
| 7.5 | Sharp | 12.0 | 59.0 | 100 | 1 Alternating | Auto |
| 7.6 | Sharp | 12.0 | 39.0 | 100 | 1 Alternating | Auto |
| 8.0 | Sharp | 61.0 | 41.0 | 100 | 1 Alternating | Auto |

-continued

| Mode Code: 0089 | | RCT Post OP | | | Type: User | |
|---|---|---|---|---|---|---|
| Seq | Waveshape | Freq1 | Freq2 | Current | Duration Polarity | Mode |
| 9.0 | Sharp | 61.0 | 59.0 | 100 | 1 Alternating | Auto |
| 9.1 | Sharp | 61.0 | 39.0 | 100 | 1 Alternating | Auto |
| 10.0 | Sharp | 284.0 | 41.0 | 100 | 1 Alternating | Auto |
| 10.1 | Sharp | 284.0 | 100.0 | 100 | 1 Alternating | Auto |
| 10.2 | Sharp | 284.0 | 783.0 | 100 | 1 Alternating | Auto |
| 11.0 | Sharp | 284.0 | 59.0 | 100 | 1 Alternating | Auto |
| 11.1 | Sharp | 284.0 | 39.0 | 100 | 1 Alternating | Auto |
| 11.9 | Sharp | 40.0 | 116.0 | 100 | 4 Alternating | Auto |
| 12.0 | Sharp | 40.0 | 41.0 | 100 | 4 Alternating | Auto |
| 12.1 | Sharp | 40.0 | 100.0 | 100 | 4 Alternating | Auto |
| 12.2 | Sharp | 40.0 | 783.0 | 100 | 4 Alternating | Auto |
| 13.0 | Sharp | 40.0 | 59.0 | 100 | 4 Alternating | Auto |
| 13.1 | Sharp | 40.0 | 39.0 | 100 | 4 Alternating | Auto |
| 14.0 | Sharp | 91.0 | 100.0 | 100 | 1 Alternating | Auto |
| 15.0 | Sharp | 91.0 | 783.0 | 100 | 3 Alternating | Auto |
| 16.0 | Sharp | 81.0 | 100.0 | 100 | 2 Alternating | Auto |
| 17.0 | Sharp | 81.0 | 783.0 | 100 | 2 Alternating | Auto |
| 18.0 | Sharp | 49.0 | 100.0 | 100 | 1 Alternating | Auto |
| 19.0 | Sharp | 49.0 | 59.0 | 100 | 1 Alternating | Auto |
| 20.0 | Sharp | 49.0 | 39.0 | 100 | 1 Alternating | Auto |
| 21.0 | Sharp | 49.0 | 783.0 | 100 | 1 Alternating | Auto |
| 28.0 | Sharp | 35.0 | 102.0 | 100 | 1 Alternating | Auto |

For background purposes, Toxic Oral Pathology Assay (TOPAS) is a chairside test, useful in clinical evaluation, for the detection of bacterial toxins, bacterial proteins, and human inflammatory proteins in gingival crevicular fluid (GCF). The TOPAS test detects two markers of infection:

Increased levels of bacterial toxins.

Increased levels of human inflammatory and serum proteins as well as bacterial proteins.

A TOPAS test assesses the presence of infection in the gums, in root canal teeth and in bone infections. It is based on the chemical reaction of a sample of fluids taken from the neck of a tooth (GCF) with specially formulated reagents.

FIG. 6 shows the results of a TOPAS GCF toxicity pre-screening assay following a root canal The patient being treated had a medical diagnosis of Hepatitis C and was experiencing unresolved pain and inflammation subsequent to root canal therapy. The root canal post op protocol was administered and the patient's pain and inflammation was eliminated. In addition, a drop in the TOPAS markers of infection was observed. Advantageously, the frequencies used for the root canal post op protocol are also being used to prevent and treat areas of osteitis in the bone around treated root canal teeth.

A frequency specific microcurrent protocol is further provided in accordance with one embodiment of the present invention for use in conjunction with treatment of chronic osteonecrosis. Preferably, the Red and Green leads 74 and 76 with adhesive pads are placed on the back of the patient's neck, and the Black and Yellow leads 72 and 78 may be attached by alligator clips to wet 4×4 gauze in the patient's mouth (with the Red lead opposite the Black lead and the Green lead opposite the Yellow lead). The preferred parameters for the chronic osteonecrosis treatment protocol have the following approximate values.

| Mode Code: 0111 | | Osteonecrosis | | | Type: User | |
|---|---|---|---|---|---|---|
| Seq | Waveshape | Freq1 | Freq2 | Current | Duration Polarity | Mode |
| 1.0 | Sharp | 58.0 | 0.1 | 100 | 1 Alternating | Auto |
| 2.0 | Sharp | 58.0 | 1.0 | 100 | 1 Alternating | Auto |
| 3.0 | Sharp | 58.0 | 2.0 | 100 | 1 Alternating | Auto |

-continued

| | Mode Code: 0111 | | Osteonecrosis | | Type: User | |
|---|---|---|---|---|---|---|
| Seq | Waveshape | Freq1 | Freq2 | Current | Duration | Polarity | Mode |
| 4.0 | Sharp | 58.0 | 32.0 | 100 | 1 | Alternating | Auto |
| 5.0 | Sharp | 60.0 | 0.1 | 100 | 1 | Alternating | Auto |
| 6.0 | Sharp | 66.0 | 0.1 | 100 | 1 | Alternating | Auto |
| 7.0 | Sharp | 64.0 | 42.0 | 100 | 1 | Alternating | Auto |
| 8.0 | Sharp | 64.0 | 63.0 | 100 | 1 | Alternating | Auto |
| 9.0 | Sharp | 460.0 | 650.0 | 100 | 1 | Alternating | Auto |
| 10.0 | Sharp | 97.0 | 40.0 | 100 | 1 | Alternating | Auto |
| 11.0 | Sharp | 98.0 | 20.0 | 100 | 1 | Alternating | Auto |
| 12.0 | Sharp | 12.0 | 59.0 | 100 | 1 | Alternating | Auto |
| 13.0 | Sharp | 12.0 | 39.0 | 100 | 1 | Alternating | Auto |
| 14.0 | Sharp | 61.0 | 59.0 | 100 | 1 | Alternating | Auto |
| 15.0 | Sharp | 61.0 | 39.0 | 100 | 1 | Alternating | Auto |
| 16.0 | Sharp | 40.0 | 116.0 | 100 | 4 | Alternating | Auto |
| 17.0 | Sharp | 40.0 | 62.0 | 100 | 4 | Alternating | Auto |
| 18.0 | Sharp | 40.0 | 59.0 | 100 | 4 | Alternating | Auto |
| 19.0 | Sharp | 40.0 | 39.0 | 100 | 4 | Alternating | Auto |
| 20.0 | Sharp | 40.0 | 783.0 | 100 | 4 | Alternating | Auto |
| 21.0 | Sharp | 40.0 | 238.0 | 100 | 1 | Alternating | Auto |
| 22.0 | Sharp | 284.0 | 62.0 | 100 | 2 | Alternating | Auto |
| 23.0 | Sharp | 284.0 | 142.0 | 100 | 2 | Alternating | Auto |
| 24.0 | Sharp | 284.0 | 59.0 | 100 | 2 | Alternating | Auto |
| 25.0 | Sharp | 284.0 | 39.0 | 100 | 2 | Alternating | Auto |
| 26.0 | Sharp | 284.0 | 783.0 | 100 | 2 | Alternating | Auto |
| 27.0 | Sharp | 284.0 | 238.0 | 100 | 1 | Alternating | Auto |
| 28.0 | Sharp | 91.0 | 142.0 | 100 | 1 | Alternating | Auto |
| 29.0 | Sharp | 91.0 | 783.0 | 100 | 3 | Alternating | Auto |
| 30.0 | Sharp | 81.0 | 142.0 | 100 | 2 | Alternating | Auto |
| 31.0 | Sharp | 81.0 | 783.0 | 100 | 2 | Alternating | Auto |
| 32.0 | Sharp | 49.0 | 62.0 | 100 | 1 | Alternating | Auto |
| 33.0 | Sharp | 49.0 | 59.0 | 100 | 1 | Alternating | Auto |
| 34.0 | Sharp | 49.0 | 39.0 | 100 | 1 | Alternating | Auto |
| 35.0 | Sharp | 49.0 | 783.0 | 100 | 1 | Alternating | Auto |

A frequency specific microcurrent protocol is further provided in accordance with one embodiment of the present invention for use in conjunction with osteonecrosis surgery post op. Preferably, the Red and Green leads 74 and 76 with adhesive pads are placed on the back of the patient's neck, and the Black and Yellow leads 72 and 78 may be attached by alligator clips to wet 4×4 gauze in the patient's mouth (with the Red lead opposite the Black lead and the Green lead opposite the Yellow lead). The preferred parameters for the osteonecrosis surgery post op protocol have the following approximate values.

| | Mode Code: 0138 | | Osteonec Post Op | | Type: User | |
|---|---|---|---|---|---|---|
| Seq | Waveshape | Freq1 | Freq2 | Current | Duration | Polarity | Mode |
| 1.0 | Gentle | 18.0 | 62.0 | 100 | 2 | Alternating | Auto |
| 2.0 | Gentle | 18.0 | 59.0 | 100 | 2 | Alternating | Auto |
| 3.0 | Gentle | 18.0 | 39.0 | 100 | 2 | Alternating | Auto |
| 4.0 | Gentle | 18.0 | 238.0 | 100 | 2 | Alternating | Auto |
| 5.0 | Sharp | 60.0 | 0.1 | 100 | 1 | Alternating | Auto |
| 6.0 | Sharp | 66.0 | 0.1 | 100 | 1 | Alternating | Auto |
| 7.0 | Sharp | 64.0 | 42.0 | 100 | 1 | Alternating | Auto |
| 8.0 | Sharp | 64.0 | 63.0 | 100 | 1 | Alternating | Auto |
| 9.0 | Sharp | 460.0 | 650.0 | 100 | 1 | Alternating | Auto |
| 10.0 | Sharp | 230.0 | 430.0 | 100 | 1 | Alternating | Auto |
| 11.0 | Sharp | 97.0 | 40.0 | 100 | 1 | Alternating | Auto |
| 12.0 | Sharp | 98.0 | 20.0 | 100 | 1 | Alternating | Auto |
| 13.0 | Sharp | 12.0 | 59.0 | 100 | 1 | Alternating | Auto |
| 14.0 | Sharp | 12.0 | 39.0 | 100 | 1 | Alternating | Auto |
| 15.0 | Sharp | 61.0 | 59.0 | 100 | 1 | Alternating | Auto |
| 16.0 | Sharp | 61.0 | 39.0 | 100 | 1 | Alternating | Auto |
| 17.0 | Gentle | 124.0 | 59.0 | 100 | 2 | Alternating | Auto |
| 18.0 | Gentle | 124.0 | 39.0 | 100 | 2 | Alternating | Auto |
| 19.0 | Gentle | 124.0 | 783.0 | 100 | 2 | Alternating | Auto |
| 20.0 | Gentle | 40.0 | 116.0 | 100 | 4 | Alternating | Auto |
| 21.0 | Gentle | 40.0 | 62.0 | 100 | 4 | Alternating | Auto |
| 22.0 | Gentle | 40.0 | 59.0 | 100 | 4 | Alternating | Auto |
| 23.0 | Gentle | 40.0 | 39.0 | 100 | 4 | Alternating | Auto |
| 24.0 | Gentle | 40.0 | 783.0 | 100 | 4 | Alternating | Auto |
| 25.0 | Gentle | 40.0 | 238.0 | 100 | 1 | Alternating | Auto |
| 26.0 | Gentle | 49.0 | 59.0 | 100 | 1 | Alternating | Auto |
| 27.0 | Gentle | 49.0 | 39.0 | 100 | 1 | Alternating | Auto |
| 28.0 | Gentle | 81.0 | 783.0 | 100 | 4 | Alternating | Auto |
| 29.0 | Gentle | 49.0 | 783.0 | 100 | 1 | Alternating | Auto |

In accordance with various additional embodiments of the present invention, frequency specific microcurrent protocols are provided in conjunction with orthodontics. A frequency specific microcurrent protocol is provided in accordance with one embodiment of the present invention for use in conjunction with prevention of pain associated with orthodontic procedures. This protocol is used after initial placement of braces and can be administered after adjustment visits to prevent pain. Preferably, the Red and Green leads 74 and 76 with adhesive pads are placed on the back of the patient's neck, and the Black and Yellow leads 72 and 78 may be attached by alligator clips to wet 4×4 gauze in the patient's mouth (with the Red lead opposite the Black lead and the Green lead opposite the Yellow lead). The preferred parameters for the protocol for prevention of pain due to orthodontic procedures have the following approximate values.

| | Mode Code: 0090 | | Ortho - pain | | Type: User | |
|---|---|---|---|---|---|---|
| Seq | Waveshape | Freq1 | Freq2 | Current | Duration | Polarity | Mode |
| 1.0 | Gentle | 18.0 | 62.0 | 100 | 3 | Alternating | Auto |
| 2.0 | Gentle | 18.0 | 396.0 | 100 | 2 | Positive | Auto |
| 3.0 | Gentle | 18.0 | 77.0 | 100 | 2 | Alternating | Auto |
| 4.0 | Gentle | 18.0 | 100.0 | 100 | 2 | Alternating | Auto |
| 5.0 | Gentle | 19.0 | 45.0 | 100 | 1 | Alternating | Auto |
| 6.0 | Gentle | 19.0 | 77.0 | 100 | 1 | Alternating | Auto |
| 7.0 | Gentle | 124.0 | 62.0 | 100 | 1 | Alternating | Auto |
| 8.0 | Gentle | 124.0 | 77.0 | 100 | 1 | Alternating | Auto |
| 9.0 | Gentle | 124.0 | 100.0 | 100 | 1 | Alternating | Auto |
| 10.0 | Gentle | 124.0 | 783.0 | 100 | 1 | Alternating | Auto |
| 11.0 | Gentle | 40.0 | 116.0 | 100 | 4 | Alternating | Auto |
| 12.0 | Gentle | 40.0 | 62.0 | 100 | 2 | Alternating | Auto |
| 13.0 | Gentle | 40.0 | 77.0 | 100 | 2 | Alternating | Auto |
| 14.0 | Gentle | 40.0 | 100.0 | 100 | 2 | Alternating | Auto |
| 15.0 | Gentle | 40.0 | 783.0 | 100 | 2 | Alternating | Auto |
| 16.0 | Gentle | 94.0 | 396.0 | 100 | 2 | Positive | Auto |
| 17.0 | Gentle | 40.0 | 396.0 | 100 | 2 | Positive | Auto |
| 18.0 | Gentle | 294.0 | 62.0 | 100 | 1 | Alternating | Auto |
| 19.0 | Gentle | 294.0 | 77.0 | 100 | 1 | Alternating | Auto |
| 20.0 | Gentle | 294.0 | 100.0 | 100 | 1 | Alternating | Auto |
| 21.0 | Gentle | 294.0 | 783.0 | 100 | 1 | Alternating | Auto |
| 22.0 | Gentle | 321.0 | 62.0 | 100 | 1 | Alternating | Auto |
| 23.0 | Gentle | 321.0 | 77.0 | 100 | 1 | Alternating | Auto |
| 24.0 | Gentle | 321.0 | 100.0 | 100 | 1 | Alternating | Auto |
| 25.0 | Gentle | 321.0 | 783.0 | 100 | 1 | Alternating | Auto |
| 26.0 | Gentle | 9.0 | 62.0 | 100 | 1 | Alternating | Auto |
| 27.0 | Gentle | 9.0 | 77.0 | 100 | 1 | Alternating | Auto |
| 28.0 | Gentle | 9.0 | 100.0 | 100 | 1 | Alternating | Auto |
| 29.0 | Gentle | 9.0 | 783.0 | 100 | 1 | Alternating | Auto |
| 30.0 | Gentle | 81.0 | 77.0 | 100 | 2 | Alternating | Auto |
| 31.0 | Gentle | 81.0 | 100.0 | 100 | 2 | Alternating | Auto |
| 32.0 | Gentle | 81.0 | 783.0 | 100 | 2 | Alternating | Auto |
| 33.0 | Gentle | 49.0 | 62.0 | 100 | 1 | Alternating | Auto |
| 34.0 | Gentle | 49.0 | 77.0 | 100 | 1 | Alternating | Auto |
| 35.0 | Gentle | 49.0 | 100.0 | 100 | 1 | Alternating | Auto |
| 36.0 | Gentle | 49.0 | 783.0 | 100 | 1 | Alternating | Auto |
| 37.0 | Gentle | 35.0 | 102.0 | 100 | 1 | Alternating | Auto |

It is preferred that the protocol for prevention of pain due to orthodontic treatment be administered within the first four hours following treatment. Advantageously, orthodontic patients have been found to experience dramatically reduced pain and soreness. Also, early observations indicate accelerated tooth movement may be occurring.

A frequency specific microcurrent protocol is also provided in accordance with one embodiment of the present invention for use in conjunction with orthodontic mid-adjustment procedures. This protocol was developed after observing what appears to be accelerated tooth movement with the above-described protocol to prevent pain associated with orthodontic procedures. The purpose of this protocol is to increase cellular activity and prevent hyalinization of the periodontal ligament, which is observed when excessive orthodontic force is applied and results in resorption of the roots of the teeth. Preferably, the Red and Green leads 74 and 76 with adhesive pads are placed on the back of the patient's neck, and the Black and Yellow leads 72 and 78 may be attached by alligator clips to wet 4×4 gauze in the patient's mouth (with the Red lead opposite the Black lead and the Green lead opposite the Yellow lead). The preferred parameters for the protocol in conjunction with mid-adjustment orthodontic procedures have the following approximate values.

| Mode Code: 0091 | | Ortho - mid adj | | | Type: User | |
|---|---|---|---|---|---|---|
| Seq | Waveshape | Freq1 | Freq2 | Current | Duration | Polarity | Mode |
| 1.0 | Sharp | 58.0 | 0.1 | 100 | 1 | Alternating | Auto |
| 2.0 | Sharp | 58.0 | 1.0 | 100 | 1 | Alternating | Auto |
| 3.0 | Sharp | 58.0 | 2.0 | 100 | 1 | Alternating | Auto |
| 4.0 | Sharp | 58.0 | 32.0 | 100 | 1 | Alternating | Auto |
| 5.0 | Sharp | 40.0 | 116.0 | 100 | 4 | Alternating | Auto |
| 6.0 | Sharp | 40.0 | 100.0 | 100 | 4 | Alternating | Auto |
| 7.0 | Sharp | 40.0 | 59.0 | 100 | 4 | Alternating | Auto |
| 8.0 | Sharp | 40.0 | 39.0 | 100 | 4 | Alternating | Auto |
| 9.0 | Sharp | 40.0 | 783.0 | 100 | 4 | Alternating | Auto |
| 10.0 | Sharp | 40.0 | 238.0 | 100 | 1 | Alternating | Auto |
| 11.0 | Sharp | 284.0 | 100.0 | 100 | 2 | Alternating | Auto |
| 13.0 | Sharp | 284.0 | 59.0 | 100 | 2 | Alternating | Auto |
| 14.0 | Sharp | 284.0 | 39.0 | 100 | 2 | Alternating | Auto |
| 15.0 | Sharp | 284.0 | 783.0 | 100 | 2 | Alternating | Auto |
| 16.0 | Sharp | 284.0 | 238.0 | 100 | 1 | Alternating | Auto |
| 17.0 | Sharp | 91.0 | 100.0 | 100 | 1 | Alternating | Auto |
| 18.0 | Sharp | 91.0 | 783.0 | 100 | 3 | Alternating | Auto |
| 19.0 | Sharp | 81.0 | 100.0 | 100 | 2 | Alternating | Auto |
| 20.0 | Sharp | 81.0 | 783.0 | 100 | 2 | Alternating | Auto |
| 21.0 | Sharp | 49.0 | 100.0 | 100 | 1 | Alternating | Auto |
| 22.0 | Sharp | 49.0 | 59.0 | 100 | 1 | Alternating | Auto |
| 23.0 | Sharp | 49.0 | 39.0 | 100 | 1 | Alternating | Auto |
| 24.0 | Sharp | 49.0 | 783.0 | 100 | 1 | Alternating | Auto |

While the foregoing description has been with reference to particular embodiments and contemplated alternative embodiments of the present invention, it will be appreciated by those skilled in the art that changes in these embodiments may be made without departing from the principles and spirit of the invention. For example, the preferred parameters for the frequency specific microcurrent protocols in accordance with the various embodiments of the present invention described above are based on a sample of patients and may differ depending on the physical condition and characteristics of a given patient. For example, as described above, the range for the amplitude of the microcurrent may vary from approximately 20 to 400 microamps depending on the sensitivity and tolerance of individual patients. Consequently, the parameters described for the various frequency specific protocols are by way of example only and are to be considered to be within a range of the parameters that would apply to the general population as will be apparent to persons skilled in the art. Accordingly, the scope of the present invention can only be ascertained with reference to the appended claims.

What is claimed is:

1. A method to selectively administer electrical stimuli to a dental patient in conjunction with preventing or treating inflammation associated with performing oral surgery or other dental procedures or orthodontic procedures, comprising:

providing a source of variable frequency, variable amplitude, variable duration electrical signals programmable according to a predetermined protocol, wherein the predetermined protocol is administered to sequentially apply a plurality of electrical signals, each electrical signal having a frequency that is programmed in a range of 0.1 to 970 hertz, an amplitude that is programmed in a range of approximately 20 to 400 microamps, and a programmed duration, wherein at least two of the electrical signals have different frequencies, amplitudes, or durations; and providing a plurality of electrodes adapted to be located to connect the source to the patient, the plurality of electrodes comprising one or more electrodes adapted to be located within the oral cavity of the patient, such that the variable frequency, variable amplitude electrical signals are applied as electrical stimuli proximate to the mouth when the predetermined protocol is being administered.

2. The method of claim 1 wherein there are first and second pairs of electrodes, each pair comprising one or more electrodes adapted to be located within the oral cavity of the patient, and the frequency of the electrical signals applied by the first pair of electrodes is programmed in a range of approximately 3.0 to 970 hertz and the amplitude is programmed in a range of approximately 20 to 400 microamps, and the frequency of the electrical signals applied by the second pair of electrodes is programmed in a range of approximately 0.1 to 783 hertz and the amplitude is programmed in a range of approximately 20 to 400 microamps.

3. The method of claim 2 wherein the protocol is for use in conjunction with gingival surgery or chronic periodontitis and wherein the frequency of the electrical signals applied by the first pair of electrodes is programmed in a range of approximately 9.0 to 321 hertz and the amplitude is programmed in a range of approximately 20 to 400 microamps, and the frequency of the electrical signals applied by the second pair of electrodes is programmed in a range of approximately 45 to 783 hertz and the amplitude is programmed in a range of approximately 20 to 400 microamps.

4. The method of claim 3 wherein parameters for the gingival surgery or chronic periodontitis protocol have the following approximate values:

| Mode Code: 0086 | | T-Ging Surgery | | | Type: User | |
|---|---|---|---|---|---|---|
| Seq | Waveshape | Freq1 | Freq2 | Current | Duration | Polarity | Mode |
| 0.9 | Gentle | 18.0 | 62.0 | 100 | 3 | Alternating | Auto |
| 1.1 | Gentle | 18.0 | 142.0 | 100 | 3 | Alternating | Auto |
| 1.2 | Gentle | 18.0 | 396.0 | 100 | 3 | Alternating | Auto |
| 1.8 | Gentle | 18.0 | 70.0 | 100 | 3 | Alternating | Auto |
| 1.9 | Gentle | 19.0 | 124.0 | 100 | 2 | Alternating | Auto |
| 2.0 | Gentle | 19.0 | 45.0 | 100 | 2 | Alternating | Auto |
| 2.1 | Gentle | 19.0 | 142.0 | 100 | 2 | Alternating | Auto |
| 3.0 | Gentle | 124.0 | 124.0 | 100 | 1 | Alternating | Auto |
| 3.1 | Gentle | 124.0 | 62.0 | 100 | 1 | Alternating | Auto |
| 4.0 | Gentle | 124.0 | 142.0 | 100 | 1 | Alternating | Auto |
| 4.1 | Gentle | 124.0 | 70.0 | 100 | 1 | Alternating | Auto |
| 5.0 | Gentle | 124.0 | 77.0 | 100 | 1 | Alternating | Auto |
| 5.1 | Gentle | 124.0 | 783.0 | 100 | 1 | Alternating | Auto |

-continued

| Mode Code: 0086 | | T-Ging Surgery | | | Type: User | |
|---|---|---|---|---|---|---|
| Seq | Waveshape | Freq1 | Freq2 | Current | Duration Polarity | Mode |
| 6.0 | Gentle | 294.0 | 62.0 | 100 | 1 Alternating | Auto |
| 7.0 | Gentle | 294.0 | 142.0 | 100 | 1 Alternating | Auto |
| 7.1 | Gentle | 294.0 | 70.0 | 100 | 1 Alternating | Auto |
| 8.0 | Gentle | 294.0 | 77.0 | 100 | 1 Alternating | Auto |
| 8.1 | Gentle | 294.0 | 783.0 | 100 | 1 Alternating | Auto |
| 9.0 | Gentle | 321.0 | 62.0 | 100 | 1 Alternating | Auto |
| 10.0 | Gentle | 321.0 | 142.0 | 100 | 1 Alternating | Auto |
| 10.1 | Gentle | 321.0 | 70.0 | 100 | 1 Alternating | Auto |
| 11.0 | Gentle | 321.0 | 77.0 | 100 | 1 Alternating | Auto |
| 11.1 | Gentle | 321.0 | 783.0 | 100 | 1 Alternating | Auto |
| 12.0 | Gentle | 9.0 | 62.0 | 100 | 1 Alternating | Auto |
| 13.0 | Gentle | 9.0 | 142.0 | 100 | 1 Alternating | Auto |
| 13.1 | Gentle | 9.0 | 70.0 | 100 | 1 Alternating | Auto |
| 14.0 | Gentle | 9.0 | 77.0 | 100 | 1 Alternating | Auto |
| 14.1 | Gentle | 9.0 | 783.0 | 100 | 1 Alternating | Auto |
| 15.0 | Gentle | 40.0 | 116.0 | 100 | 4 Alternating | Auto |
| 16.0 | Gentle | 40.0 | 142.0 | 100 | 4 Alternating | Auto |
| 17.0 | Gentle | 40.0 | 62.0 | 100 | 4 Alternating | Auto |
| 17.1 | Gentle | 40.0 | 77.0 | 100 | 4 Alternating | Auto |
| 17.1 | Gentle | 40.0 | 70.0 | 100 | 4 Alternating | Auto |
| 17.2 | Gentle | 40.0 | 783.0 | 100 | 4 Alternating | Auto |
| 18.0 | Gentle | 81.0 | 142.0 | 100 | 3 Alternating | Auto |
| 18.2 | Gentle | 81.0 | 77.0 | 100 | 3 Alternating | Auto |
| 18.3 | Gentle | 81.0 | 70.0 | 100 | 3 Alternating | Auto |
| 19.0 | Gentle | 49.0 | 62.0 | 100 | 1 Alternating | Auto |
| 20.0 | Gentle | 49.0 | 142.0 | 100 | 1 Alternating | Auto |
| 21.0 | Gentle | 49.0 | 77.0 | 100 | 1 Alternating | Auto |
| 22.0 | Gentle | 49.0 | 70.0 | 100 | 1 Alternating | Auto, | wherein Seq is a number corresponding to a sequential step in the protocol, Waveshape is selected from among the group of waveshapes consisting of gentle, mild, sharp, and pulse waveslopes, Freq1 is a first frequency in hertz of an electrical signal applied to the first pair of electrodes, Freq2 is a second frequency in hertz of an electrical signal applied to the second pair of electrodes, Current is an amperage of the electrical signals in microamps, Duration is a time in minutes, Polarity is selected from among the group of polarities consisting of positive, negative, and alternating, and Mode is set to automatically perform the protocol.

5. The method of claim 2 wherein the protocol is for use in conjunction with implant/osseous surgery and wherein the frequency of the electrical signals applied by the first pair of electrodes is programmed in a range of approximately 9.0 to 321 hertz and the amplitude is programmed in a range of approximately 20 to 400 microamps, and the frequency of the electrical signals applied by the second pair of electrodes is programmed in a range of approximately 39 to 783 hertz and the amplitude is programmed in a range of approximately 20 to 400 microamps.

6. The method of claim 5 wherein parameters for the implant/osseous surgery protocol have the following approximate values:

| Mode Code: 0094 | | T-Implant Surg | | | Type: User | |
|---|---|---|---|---|---|---|
| Seq | Waveshape | Freq1 | Freq2 | Current | Duration Polarity | Mode |
| 0.9 | Gentle | 18.0 | 124.0 | 100 | 3 Alternating | Auto |
| 1.1 | Gentle | 18.0 | 142.0 | 100 | 3 Alternating | Auto |
| 1.2 | Gentle | 18.0 | 396.0 | 100 | 3 Alternating | Auto |
| 1.8 | Gentle | 18.0 | 70.0 | 100 | 3 Alternating | Auto |
| 1.9 | Gentle | 19.0 | 124.0 | 100 | 2 Alternating | Auto |
| 2.0 | Gentle | 19.0 | 45.0 | 100 | 2 Alternating | Auto |
| 2.1 | Gentle | 19.0 | 142.0 | 100 | 2 Alternating | Auto |
| 3.0 | Gentle | 124.0 | 124.0 | 100 | 1 Alternating | Auto |
| 3.1 | Gentle | 124.0 | 62.0 | 100 | 1 Alternating | Auto |

-continued

| Mode Code: 0094 | | T-Implant Surg | | | Type: User | |
|---|---|---|---|---|---|---|
| Seq | Waveshape | Freq1 | Freq2 | Current | Duration Polarity | Mode |
| 4.0 | Gentle | 124.0 | 142.0 | 100 | 1 Alternating | Auto |
| 4.1 | Gentle | 124.0 | 70.0 | 100 | 1 Alternating | Auto |
| 5.0 | Gentle | 124.0 | 77.0 | 100 | 1 Alternating | Auto |
| 5.1 | Gentle | 124.0 | 783.0 | 100 | 2 Alternating | Auto |
| 5.2 | Gentle | 124.0 | 59.0 | 100 | 2 Alternating | Auto |
| 5.3 | Gentle | 124.0 | 39.0 | 100 | 2 Alternating | Auto |
| 6.0 | Gentle | 294.0 | 62.0 | 100 | 1 Alternating | Auto |
| 7.0 | Gentle | 294.0 | 142.0 | 100 | 1 Alternating | Auto |
| 7.1 | Gentle | 294.0 | 70.0 | 100 | 1 Alternating | Auto |
| 8.0 | Gentle | 294.0 | 77.0 | 100 | 1 Alternating | Auto |
| 8.1 | Gentle | 294.0 | 783.0 | 100 | 1 Alternating | Auto |
| 9.0 | Gentle | 321.0 | 62.0 | 100 | 1 Alternating | Auto |
| 10.0 | Gentle | 321.0 | 142.0 | 100 | 1 Alternating | Auto |
| 10.1 | Gentle | 321.0 | 70.0 | 100 | 1 Alternating | Auto |
| 11.0 | Gentle | 321.0 | 77.0 | 100 | 1 Alternating | Auto |
| 11.1 | Gentle | 321.0 | 783.0 | 100 | 1 Alternating | Auto |
| 12.0 | Gentle | 9.0 | 62.0 | 100 | 1 Alternating | Auto |
| 13.0 | Gentle | 9.0 | 142.0 | 100 | 1 Alternating | Auto |
| 13.1 | Gentle | 9.0 | 70.0 | 100 | 1 Alternating | Auto |
| 14.0 | Gentle | 9.0 | 77.0 | 100 | 1 Alternating | Auto |
| 14.1 | Gentle | 9.0 | 783.0 | 100 | 1 Alternating | Auto |
| 15.0 | Gentle | 40.0 | 116.0 | 100 | 4 Alternating | Auto |
| 16.0 | Gentle | 40.0 | 142.0 | 100 | 4 Alternating | Auto |
| 17.0 | Gentle | 40.0 | 62.0 | 100 | 4 Alternating | Auto |
| 17.1 | Gentle | 40.0 | 77.0 | 100 | 4 Alternating | Auto |
| 17.1 | Gentle | 40.0 | 70.0 | 100 | 4 Alternating | Auto |
| 17.2 | Gentle | 40.0 | 783.0 | 100 | 4 Alternating | Auto |
| 17.3 | Gentle | 40.0 | 59.0 | 100 | 4 Alternating | Auto |
| 17.4 | Gentle | 40.0 | 39.0 | 100 | 4 Alternating | Auto |
| 18.0 | Gentle | 81.0 | 142.0 | 100 | 3 Alternating | Auto |
| 18.2 | Gentle | 81.0 | 77.0 | 100 | 3 Alternating | Auto |
| 18.3 | Gentle | 81.0 | 70.0 | 100 | 3 Alternating | Auto |
| 19.0 | Gentle | 49.0 | 62.0 | 100 | 1 Alternating | Auto |
| 20.0 | Gentle | 49.0 | 142.0 | 100 | 1 Alternating | Auto |
| 21.0 | Gentle | 49.0 | 77.0 | 100 | 1 Alternating | Auto |
| 22.0 | Gentle | 49.0 | 70.0 | 100 | 1 Alternating | Auto |
| 23.0 | Gentle | 49.0 | 59.0 | 100 | 1 Alternating | Auto |
| 24.0 | Gentle | 49.0 | 39.0 | 100 | 1 Alternating | Auto |
| 25.0 | Gentle | 81.0 | 783.0 | 100 | 3 Alternating | Auto |
| 26.0 | Gentle | 49.0 | 39.0 | 100 | 1 Alternating | Auto, | wherein Seq is a number corresponding to a sequential step in the protocol, Waveshape is selected from among the group of waveshapes consisting of gentle, mild, sharp, and pulse waveslopes, Freq1 is a first frequency in hertz of an electrical signal applied to the first pair of electrodes, Freq2 is a second frequency in hertz of an electrical signal applied to the second pair of electrodes, Current is an amperage of the electrical signals in microamps, Duration is a time in minutes, Polarity is selected from among the group of polarities consisting of positive, negative, and alternating, and Mode is set to automatically perform the protocol.

7. The method of claim 2 wherein the protocol is for use in conjunction with general post operative trauma and wherein the frequency of the electrical signals applied by the first pair of electrodes is programmed in a range of approximately 6.8 to 970 hertz and the amplitude is programmed in a range of approximately 20 to 400 microamps, and the frequency of the electrical signals applied by the second pair of electrodes is programmed in a range of approximately 0.1 to 783 hertz and the amplitude is programmed in a range of approximately 20 to 400 microamps.

8. The method of claim 7 wherein parameters for the general post operative trauma protocol have the following approximate values:

| Mode Code: 0088 | | T-Post Op | | Type: User | | |
|---|---|---|---|---|---|---|
| Seq | Waveshape | Freq1 | Freq2 | Current | Duration | Polarity | Mode |
| 1.0 | Sharp | 94.0 | 200.0 | 100 | 1 | Alternating | Auto |
| 2.0 | Sharp | 970.0 | 13.0 | 100 | 1 | Alternating | Auto |
| 3.0 | Sharp | 970.0 | 200.0 | 100 | 1 | Alternating | Auto |
| 4.0 | Sharp | 94.0 | 94.0 | 100 | 1 | Alternating | Auto |
| 5.0 | Sharp | 6.8 | 38.0 | 100 | 1 | Alternating | Auto |
| 6.0 | Sharp | 60.0 | 0.1 | 100 | 1 | Alternating | Auto |
| 7.0 | Sharp | 66.0 | 0.1 | 100 | 1 | Alternating | Auto |
| 8.0 | Sharp | 64.0 | 42.0 | 100 | 1 | Alternating | Auto |
| 9.0 | Sharp | 64.0 | 63.0 | 100 | 1 | Alternating | Auto |
| 10.0 | Gentle | 18.0 | 62.0 | 100 | 3 | Alternating | Auto |
| 11.0 | Gentle | 18.0 | 142.0 | 100 | 2 | Alternating | Auto |
| 12.0 | Gentle | 18.0 | 396.0 | 100 | 2 | Alternating | Auto |
| 13.0 | Gentle | 19.0 | 45.0 | 100 | 2 | Alternating | Auto |
| 14.0 | Gentle | 19.0 | 142.0 | 100 | 2 | Alternating | Auto |
| 15.0 | Gentle | 124.0 | 62.0 | 100 | 1 | Alternating | Auto |
| 16.0 | Gentle | 124.0 | 142.0 | 100 | 1 | Alternating | Auto |
| 17.0 | Gentle | 124.0 | 191.0 | 100 | 1 | Alternating | Auto |
| 18.0 | Gentle | 124.0 | 783.0 | 100 | 1 | Alternating | Auto |
| 19.0 | Gentle | 124.0 | 243.0 | 100 | 1 | Alternating | Auto |
| 20.0 | Gentle | 40.0 | 62.0 | 100 | 2 | Alternating | Auto |
| 21.0 | Gentle | 40.0 | 142.0 | 100 | 2 | Alternating | Auto |
| 22.0 | Gentle | 40.0 | 191.0 | 100 | 2 | Alternating | Auto |
| 23.0 | Gentle | 40.0 | 783.0 | 100 | 2 | Alternating | Auto |
| 24.0 | Gentle | 40.0 | 243.0 | 100 | 2 | Alternating | Auto |
| 24.1 | Gentle | 40.0 | 41.0 | 100 | 2 | Alternating | Auto |
| 25.0 | Gentle | 94.0 | 396.0 | 100 | 1 | Alternating | Auto |
| 26.0 | Gentle | 40.0 | 396.0 | 100 | 1 | Alternating | Auto |
| 27.0 | Gentle | 294.0 | 41.0 | 100 | 1 | Alternating | Auto |
| 28.0 | Gentle | 321.0 | 41.0 | 100 | 1 | Alternating | Auto |
| 29.0 | Gentle | 9.0 | 41.0 | 100 | 1 | Alternating | Auto |
| 30.0 | Gentle | 294.0 | 62.0 | 100 | 1 | Alternating | Auto |
| 31.0 | Gentle | 321.0 | 62.0 | 100 | 1 | Alternating | Auto |
| 32.0 | Gentle | 9.0 | 62.0 | 100 | 1 | Alternating | Auto |
| 33.0 | Gentle | 49.0 | 62.0 | 100 | 1 | Alternating | Auto |
| 34.0 | Gentle | 81.0 | 142.0 | 100 | 2 | Alternating | Auto |
| 35.0 | Gentle | 49.0 | 142.0 | 100 | 1 | Alternating | Auto, | wherein Seq is a number corresponding to a sequential step in the protocol, Waveshape is selected from among the group of waveshapes consisting of gentle, mild, sharp, and pulse waveslopes, Freq1 is a first frequency in hertz of an electrical signal applied to the first pair of electrodes, Freq2 is a second frequency in hertz of an electrical signal applied to the second pair of electrodes, Current is an amperage of the electrical signals in microamps, Duration is a time in minutes, Polarity is selected from among the group of polarities consisting of positive, negative, and alternating, and Mode is set to automatically perform the protocol.

9. The method of claim 2 wherein the protocol is for use in conjunction with pulpal trauma and wherein the frequency of the electrical signals applied by the first pair of electrodes is programmed in a range of approximately 6.8 to 970 hertz and the amplitude is programmed in a range of approximately 20 to 400 microamps, and the frequency of the electrical signals applied by the second pair of electrodes is programmed in a range of approximately 0.1 to 783 hertz and the amplitude is programmed in a range of approximately 20 to 400 microamps.

10. The method of claim 9 wherein parameters for the pulpal trauma protocol have the following approximate values:

| Mode Code: 0093 | | Pulpal Trauma A | | Type: User | | |
|---|---|---|---|---|---|---|
| Seq | Waveshape | Freq1 | Freq2 | Current | Duration | Polarity | Mode |
| 1.0 | Gentle | 94.0 | 200.0 | 100 | 1 | Alternating | Auto |
| 2.0 | Gentle | 94.0 | 94.0 | 100 | 1 | Alternating | Auto |
| 3.0 | Gentle | 94.0 | 45.0 | 100 | 1 | Alternating | Auto |
| 4.0 | Gentle | 970.0 | 200.0 | 100 | 1 | Alternating | Auto |
| 5.0 | Gentle | 6.8 | 38.0 | 100 | 1 | Alternating | Auto |
| 6.0 | Gentle | 60.0 | 0.1 | 100 | 1 | Alternating | Auto |
| 7.0 | Gentle | 66.0 | 0.1 | 100 | 1 | Alternating | Auto |
| 8.0 | Gentle | 64.0 | 42.0 | 100 | 1 | Alternating | Auto |
| 9.0 | Gentle | 64.0 | 63.0 | 100 | 1 | Alternating | Auto |
| 10.0 | Gentle | 97.0 | 40.0 | 100 | 1 | Alternating | Auto |
| 11.0 | Gentle | 98.0 | 20.0 | 100 | 1 | Alternating | Auto |
| 12.0 | Gentle | 18.0 | 62.0 | 100 | 3 | Alternating | Auto |
| 13.0 | Gentle | 19.0 | 45.0 | 100 | 2 | Alternating | Auto |
| 14.0 | Gentle | 124.0 | 396.0 | 100 | 1 | Alternating | Auto |
| 15.0 | Gentle | 124.0 | 62.0 | 100 | 1 | Alternating | Auto |
| 16.0 | Gentle | 124.0 | 41.0 | 100 | 1 | Alternating | Auto |
| 17.0 | Gentle | 124.0 | 77.0 | 100 | 1 | Alternating | Auto |
| 18.0 | Gentle | 124.0 | 100.0 | 100 | 1 | Alternating | Auto |
| 19.0 | Gentle | 294.0 | 396.0 | 100 | 1 | Alternating | Auto |
| 20.0 | Gentle | 294.0 | 62.0 | 100 | 1 | Alternating | Auto |
| 21.0 | Gentle | 294.0 | 41.0 | 100 | 1 | Alternating | Auto |
| 22.0 | Gentle | 294.0 | 77.0 | 100 | 1 | Alternating | Auto |
| 23.0 | Gentle | 294.0 | 100.0 | 100 | 1 | Alternating | Auto |
| 24.0 | Gentle | 321.0 | 396.0 | 100 | 1 | Alternating | Auto |
| 25.0 | Gentle | 321.0 | 62.0 | 100 | 1 | Alternating | Auto |
| 26.0 | Gentle | 321.0 | 41.0 | 100 | 1 | Alternating | Auto |
| 27.0 | Gentle | 321.0 | 77.0 | 100 | 1 | Alternating | Auto |
| 28.0 | Gentle | 321.0 | 100.0 | 100 | 1 | Alternating | Auto |
| 29.0 | Gentle | 9.0 | 396.0 | 100 | 1 | Alternating | Auto |
| 30.0 | Gentle | 9.0 | 62.0 | 100 | 1 | Alternating | Auto |
| 31.0 | Gentle | 9.0 | 41.0 | 100 | 1 | Alternating | Auto |
| 32.0 | Gentle | 9.0 | 77.0 | 100 | 1 | Alternating | Auto |
| 33.0 | Gentle | 9.0 | 100.0 | 100 | 1 | Alternating | Auto |
| 34.0 | Gentle | 40.0 | 116.0 | 100 | 4 | Alternating | Auto |
| 35.0 | Gentle | 40.0 | 396.0 | 100 | 4 | Alternating | Auto |
| 36.0 | Gentle | 40.0 | 41.0 | 100 | 4 | Alternating | Auto |
| 37.0 | Gentle | 40.0 | 62.0 | 100 | 4 | Alternating | Auto |
| 38.0 | Gentle | 40.0 | 77.0 | 100 | 1 | Alternating | Auto |
| 39.0 | Gentle | 40.0 | 100.0 | 100 | 1 | Alternating | Auto |
| 40.0 | Gentle | 40.0 | 396.0 | 100 | 4 | Alternating | Auto |
| 41.0 | Gentle | 49.0 | 396.0 | 100 | 1 | Alternating | Auto |
| 42.0 | Gentle | 49.0 | 62.0 | 100 | 1 | Alternating | Auto |
| 43.0 | Gentle | 49.0 | 41.0 | 100 | 1 | Alternating | Auto |
| 44.0 | Gentle | 49.0 | 77.0 | 100 | 1 | Alternating | Auto, | wherein Seq is a number corresponding to a sequential step in the protocol, Waveshape is selected from among the group of waveshapes consisting of gentle, mild, sharp, and pulse waveslopes, Freq1 is a first frequency in hertz of an electrical signal applied to the first pair of electrodes, Freq2 is a second frequency in hertz of an electrical signal applied to the second pair of electrodes, Current is an amperage of the electrical signals in microamps, Duration is a time in minutes, Polarity is selected from among the group of polarities consisting of positive, negative, and alternating, and Mode is set to automatically perform the protocol.

11. The method of claim 2 wherein the protocol is for use in conjunction with pulpal inflammation and wherein the frequency of the electrical signals applied by the first pair of electrodes is programmed in a range of approximately 6.8 to 970 hertz and the amplitude is programmed in a range of approximately 20 to 400 microamps, and the frequency of the electrical signals applied by the second pair of electrodes is programmed in a range of approximately 0.1 to 396 hertz and the amplitude is programmed in a range of approximately 20 to 400 microamps.

12. The method of claim 11 wherein parameters for the pulpal inflammation protocol have the following approximate values:

| Mode Code: 0087 | | Pulpal Inflamm | | Type: User | | |
|---|---|---|---|---|---|---|
| Seq | Waveshape | Freq1 | Freq2 | Current | Duration | Polarity | Mode |
| 1.0 | Sharp | 94.0 | 200.0 | 100 | 1 | Alternating | Auto |
| 2.0 | Sharp | 970.0 | 200.0 | 100 | 1 | Alternating | Auto |
| 3.0 | Sharp | 6.8 | 38.0 | 100 | 1 | Alternating | Auto |
| 4.0 | Sharp | 60.0 | 0.1 | 100 | 1 | Alternating | Auto |
| 5.0 | Sharp | 66.0 | 0.1 | 100 | 1 | Alternating | Auto |
| 6.0 | Sharp | 64.0 | 42.0 | 100 | 1 | Alternating | Auto |
| 7.0 | Sharp | 64.0 | 63.0 | 100 | 1 | Alternating | Auto |
| 8.0 | Sharp | 97.0 | 40.0 | 100 | 1 | Alternating | Auto |
| 9.0 | Sharp | 98.0 | 20.0 | 100 | 1 | Alternating | Auto |
| 10.0 | Sharp | 40.0 | 396.0 | 100 | 20 | Positive | Auto |
| 11.0 | Sharp | 284.0 | 396.0 | 100 | 5 | Positive | Auto |
| 12.0 | Sharp | 18.0 | 396.0 | 100 | 2 | Positive | Auto |
| 13.0 | Sharp | 94.0 | 396.0 | 100 | 1 | Positive | Auto |
| 14.0 | Sharp | 124.0 | 396.0 | 100 | 1 | Positive | Auto |
| 15.0 | Sharp | 321.0 | 396.0 | 100 | 1 | Positive | Auto |
| 16.0 | Sharp | 9.0 | 396.0 | 100 | 1 | Positive | Auto |
| 17.0 | Sharp | 3.0 | 396.0 | 100 | 2 | Positive | Auto |
| 18.0 | Sharp | 13.0 | 396.0 | 100 | 2 | Positive | Auto |
| 19.0 | Sharp | 91.0 | 396.0 | 100 | 2 | Positive | Auto |
| 20.0 | Sharp | 40.0 | 62.0 | 100 | 4 | Alternating | Auto |
| 21.0 | Sharp | 284.0 | 62.0 | 100 | 2 | Alternating | Auto |
| 22.0 | Sharp | 124.0 | 62.0 | 100 | 1 | Alternating | Auto |
| 23.0 | Sharp | 321.0 | 62.0 | 100 | 1 | Alternating | Auto |
| 24.0 | Sharp | 9.0 | 62.0 | 100 | 1 | Alternating | Auto |
| 25.0 | Sharp | 91.0 | 62.0 | 100 | 2 | Alternating | Auto |
| 25.1 | Sharp | 50.0 | 13.0 | 100 | 1 | Positive | Auto |
| 25.2 | Sharp | 81.0 | 13.0 | 100 | 1 | Positive | Auto |
| 25.3 | Sharp | 50.0 | 13.0 | 100 | 1 | Positive | Auto |
| 25.4 | Sharp | 81.0 | 13.0 | 100 | 1 | Positive | Auto |
| 25.5 | Sharp | 50.0 | 13.0 | 100 | 1 | Positive | Auto |
| 26.0 | Sharp | 81.0 | 396.0 | 100 | 2 | Positive | Auto |
| 27.0 | Sharp | 49.0 | 396.0 | 100 | 1 | Positive | Auto, | wherein Seq is a number corresponding to a sequential step in the protocol, Waveshape is selected from among the group of waveshapes consisting of gentle, mild, sharp, and pulse waveslopes, Freq1 is a first frequency in hertz of an electrical signal applied to the first pair of electrodes, Freq2 is a second frequency in hertz of an electrical signal applied to the second pair of electrodes, Current is an amperage of the electrical signals in microamps, Duration is a time in minutes, Polarity is selected from among the group of polarities consisting of positive, negative, and alternating, and Mode is set to automatically perform the protocol.

13. The method of claim 2 wherein the protocol is for use in conjunction with root canal post op and wherein the frequency of the electrical signals applied by the first pair of electrodes is programmed in a range of approximately 6.8 to 970 hertz and the amplitude is programmed in a range of approximately 20 to 400 microamps, and the frequency of the electrical signals applied by the second pair of electrodes is programmed in a range of approximately 0.1 to 783 hertz and the amplitude is programmed in a range of approximately 20 to 400 microamps.

14. The method of claim 13 wherein parameters for the root canal post op protocol have the following approximate values:

| Mode Code: 0089 | | RCT Post OP | | Type: User | | |
|---|---|---|---|---|---|---|
| Seq | Waveshape | Freq1 | Freq2 | Current | Duration | Polarity | Mode |
| 1.0 | Sharp | 94.0 | 200.0 | 100 | 1 | Alternating | Auto |
| 2.0 | Sharp | 970.0 | 200.0 | 100 | 1 | Alternating | Auto |
| 3.0 | Sharp | 970.0 | 13.0 | 100 | 1 | Alternating | Auto |
| 4.0 | Sharp | 94.0 | 94.0 | 100 | 1 | Alternating | Auto |
| 5.0 | Sharp | 6.8 | 38.0 | 100 | 2 | Alternating | Auto |
| 5.1 | Sharp | 60.0 | 0.1 | 100 | 1 | Alternating | Auto |

-continued

| Mode Code: 0089 | | RCT Post OP | | Type: User | | |
|---|---|---|---|---|---|---|
| Seq | Waveshape | Freq1 | Freq2 | Current | Duration | Polarity | Mode |
| 5.2 | Sharp | 66.0 | 0.1 | 100 | 1 | Alternating | Auto |
| 6.0 | Sharp | 64.0 | 42.0 | 100 | 1 | Alternating | Auto |
| 7.0 | Sharp | 64.0 | 63.0 | 100 | 1 | Alternating | Auto |
| 7.1 | Sharp | 460.0 | 650.0 | 100 | 1 | Alternating | Auto |
| 7.2 | Sharp | 97.0 | 40.0 | 100 | 1 | Alternating | Auto |
| 7.3 | Sharp | 98.0 | 20.0 | 100 | 1 | Alternating | Auto |
| 7.4 | Sharp | 12.0 | 41.0 | 100 | 1 | Alternating | Auto |
| 7.5 | Sharp | 12.0 | 59.0 | 100 | 1 | Alternating | Auto |
| 7.6 | Sharp | 12.0 | 39.0 | 100 | 1 | Alternating | Auto |
| 8.0 | Sharp | 61.0 | 41.0 | 100 | 1 | Alternating | Auto |
| 9.0 | Sharp | 61.0 | 59.0 | 100 | 1 | Alternating | Auto |
| 9.1 | Sharp | 61.0 | 39.0 | 100 | 1 | Alternating | Auto |
| 10.0 | Sharp | 284.0 | 41.0 | 100 | 1 | Alternating | Auto |
| 10.1 | Sharp | 284.0 | 100.0 | 100 | 1 | Alternating | Auto |
| 10.2 | Sharp | 284.0 | 783.0 | 100 | 1 | Alternating | Auto |
| 11.0 | Sharp | 284.0 | 59.0 | 100 | 1 | Alternating | Auto |
| 11.1 | Sharp | 284.0 | 39.0 | 100 | 1 | Alternating | Auto |
| 11.9 | Sharp | 40.0 | 116.0 | 100 | 4 | Alternating | Auto |
| 12.0 | Sharp | 40.0 | 41.0 | 100 | 4 | Alternating | Auto |
| 12.1 | Sharp | 40.0 | 100.0 | 100 | 4 | Alternating | Auto |
| 12.2 | Sharp | 40.0 | 783.0 | 100 | 4 | Alternating | Auto |
| 13.0 | Sharp | 40.0 | 59.0 | 100 | 4 | Alternating | Auto |
| 13.1 | Sharp | 40.0 | 39.0 | 100 | 4 | Alternating | Auto |
| 14.0 | Sharp | 91.0 | 100.0 | 100 | 1 | Alternating | Auto |
| 15.0 | Sharp | 91.0 | 783.0 | 100 | 3 | Alternating | Auto |
| 16.0 | Sharp | 81.0 | 100.0 | 100 | 2 | Alternating | Auto |
| 17.0 | Sharp | 81.0 | 783.0 | 100 | 2 | Alternating | Auto |
| 18.0 | Sharp | 49.0 | 100.0 | 100 | 1 | Alternating | Auto |
| 19.0 | Sharp | 49.0 | 59.0 | 100 | 1 | Alternating | Auto |
| 20.0 | Sharp | 49.0 | 39.0 | 100 | 1 | Alternating | Auto |
| 21.0 | Sharp | 49.0 | 783.0 | 100 | 1 | Alternating | Auto |
| 28.0 | Sharp | 35.0 | 102.0 | 100 | 1 | Alternating | Auto, | wherein Seq is a number corresponding to a sequential step in the protocol, Waveshape is selected from among the group of waveshapes consisting of gentle, mild, sharp, and pulse waveslopes, Freq1 is a first frequency in hertz of an electrical signal applied to the first pair of electrodes, Freq2 is a second frequency in hertz of an electrical signal applied to the second pair of electrodes, Current is an amperage of the electrical signals in microamps, Duration is a time in minutes, Polarity is selected from among the group of polarities consisting of positive, negative, and alternating, and Mode is set to automatically perform the protocol.

15. The method of claim 2 wherein the protocol is for use in conjunction with treatment of chronic osteonecrosis and wherein the frequency of the electrical signals applied by the first pair of electrodes is programmed in a range of approximately 12 to 460 hertz and the amplitude is programmed in a range of approximately 20 to 400 microamps, and the frequency of the electrical signals applied by the second pair of electrodes is programmed in a range of approximately 0.1 to 783 hertz and the amplitude is programmed in a range of approximately 20 to 400 microamps.

16. The method of claim 15 wherein parameters for the chronic osteonecrosis treatment protocol have the following approximate values:

| Mode Code: 0111 | | Osteonecrosis | | Type: User | | |
|---|---|---|---|---|---|---|
| Seq | Waveshape | Freq1 | Freq2 | Current | Duration | Polarity | Mode |
| 1.0 | Sharp | 58.0 | 0.1 | 100 | 1 | Alternating | Auto |
| 2.0 | Sharp | 58.0 | 1.0 | 100 | 1 | Alternating | Auto |
| 3.0 | Sharp | 58.0 | 2.0 | 100 | 1 | Alternating | Auto |
| 4.0 | Sharp | 58.0 | 32.0 | 100 | 1 | Alternating | Auto |
| 5.0 | Sharp | 60.0 | 0.1 | 100 | 1 | Alternating | Auto |

| Mode Code: 0111 | | Osteonecrosis | | | Type: User | |
|---|---|---|---|---|---|---|
| Seq | Waveshape | Freq1 | Freq2 | Current | Duration | Polarity | Mode |
| 6.0 | Sharp | 66.0 | 0.1 | 100 | 1 | Alternating | Auto |
| 7.0 | Sharp | 64.0 | 42.0 | 100 | 1 | Alternating | Auto |
| 8.0 | Sharp | 64.0 | 63.0 | 100 | 1 | Alternating | Auto |
| 9.0 | Sharp | 460.0 | 650.0 | 100 | 1 | Alternating | Auto |
| 10.0 | Sharp | 97.0 | 40.0 | 100 | 1 | Alternating | Auto |
| 11.0 | Sharp | 98.0 | 20.0 | 100 | 1 | Alternating | Auto |
| 12.0 | Sharp | 12.0 | 59.0 | 100 | 1 | Alternating | Auto |
| 13.0 | Sharp | 12.0 | 39.0 | 100 | 1 | Alternating | Auto |
| 14.0 | Sharp | 61.0 | 59.0 | 100 | 1 | Alternating | Auto |
| 15.0 | Sharp | 61.0 | 39.0 | 100 | 1 | Alternating | Auto |
| 16.0 | Sharp | 40.0 | 116.0 | 100 | 4 | Alternating | Auto |
| 17.0 | Sharp | 40.0 | 62.0 | 100 | 4 | Alternating | Auto |
| 18.0 | Sharp | 40.0 | 59.0 | 100 | 4 | Alternating | Auto |
| 19.0 | Sharp | 40.0 | 39.0 | 100 | 4 | Alternating | Auto |
| 20.0 | Sharp | 40.0 | 783.0 | 100 | 4 | Alternating | Auto |
| 21.0 | Sharp | 40.0 | 238.0 | 100 | 1 | Alternating | Auto |
| 22.0 | Sharp | 284.0 | 62.0 | 100 | 2 | Alternating | Auto |
| 23.0 | Sharp | 284.0 | 142.0 | 100 | 2 | Alternating | Auto |
| 24.0 | Sharp | 284.0 | 59.0 | 100 | 2 | Alternating | Auto |
| 25.0 | Sharp | 284.0 | 39.0 | 100 | 2 | Alternating | Auto |
| 26.0 | Sharp | 284.0 | 783.0 | 100 | 2 | Alternating | Auto |
| 27.0 | Sharp | 284.0 | 238.0 | 100 | 1 | Alternating | Auto |
| 28.0 | Sharp | 91.0 | 142.0 | 100 | 1 | Alternating | Auto |
| 29.0 | Sharp | 91.0 | 783.0 | 100 | 3 | Alternating | Auto |
| 30.0 | Sharp | 81.0 | 142.0 | 100 | 2 | Alternating | Auto |
| 31.0 | Sharp | 81.0 | 783.0 | 100 | 2 | Alternating | Auto |
| 32.0 | Sharp | 49.0 | 62.0 | 100 | 1 | Alternating | Auto |
| 33.0 | Sharp | 49.0 | 59.0 | 100 | 1 | Alternating | Auto |
| 34.0 | Sharp | 49.0 | 39.0 | 100 | 1 | Alternating | Auto |
| 35.0 | Sharp | 49.0 | 783.0 | 100 | 1 | Alternating | Auto, | wherein Seq is a number corresponding to a sequential step in the protocol, Waveshape is selected from among the group of waveshapes consisting of gentle, mild, sharp, and pulse waveslopes, Freq1 is a first frequency in hertz of an electrical signal applied to the first pair of electrodes, Freq2 is a second frequency in hertz of an electrical signal applied to the second pair of electrodes, Current is an amperage of the electrical signals in microamps, Duration is a time in minutes, Polarity is selected from among the group of polarities consisting of positive, negative, and alternating, and Mode is set to automatically perform the protocol.

17. The method of claim 2 wherein the protocol is for use in conjunction with osteonecrosis surgery post op and wherein the frequency of the electrical signals applied by the first pair of electrodes is programmed in a range of approximately 12 to 460 hertz and the amplitude is programmed in a range of approximately 20 to 400 microamps, and the frequency of the electrical signals applied by the second pair of electrodes is programmed in a range of approximately 0.1 to 783 hertz and the amplitude is programmed in a range of approximately 20 to 400 microamps.

18. The method of claim 17 wherein parameters for the osteonecrosis surgery post op protocol have the following approximate values:

| Mode Code: 0138 | | Osteonec Post Op | | | Type: User | |
|---|---|---|---|---|---|---|
| Seq | Waveshape | Freq1 | Freq2 | Current | Duration | Polarity | Mode |
| 1.0 | Gentle | 18.0 | 62.0 | 100 | 2 | Alternating | Auto |
| 2.0 | Gentle | 18.0 | 59.0 | 100 | 2 | Alternating | Auto |
| 3.0 | Gentle | 18.0 | 39.0 | 100 | 2 | Alternating | Auto |
| 4.0 | Gentle | 18.0 | 238.0 | 100 | 2 | Alternating | Auto |
| 5.0 | Sharp | 60.0 | 0.1 | 100 | 1 | Alternating | Auto |
| 6.0 | Sharp | 66.0 | 0.1 | 100 | 1 | Alternating | Auto |
| 7.0 | Sharp | 64.0 | 42.0 | 100 | 1 | Alternating | Auto |
| 8.0 | Sharp | 64.0 | 63.0 | 100 | 1 | Alternating | Auto |
| 9.0 | Sharp | 460.0 | 650.0 | 100 | 1 | Alternating | Auto |
| 10.0 | Sharp | 230.0 | 430.0 | 100 | 1 | Alternating | Auto |
| 11.0 | Sharp | 97.0 | 40.0 | 100 | 1 | Alternating | Auto |
| 12.0 | Sharp | 98.0 | 20.0 | 100 | 1 | Alternating | Auto |
| 13.0 | Sharp | 12.0 | 59.0 | 100 | 1 | Alternating | Auto |
| 14.0 | Sharp | 12.0 | 39.0 | 100 | 1 | Alternating | Auto |
| 15.0 | Sharp | 61.0 | 59.0 | 100 | 1 | Alternating | Auto |
| 16.0 | Sharp | 61.0 | 39.0 | 100 | 1 | Alternating | Auto |
| 17.0 | Gentle | 124.0 | 59.0 | 100 | 2 | Alternating | Auto |
| 18.0 | Gentle | 124.0 | 39.0 | 100 | 2 | Alternating | Auto |
| 19.0 | Gentle | 124.0 | 783.0 | 100 | 2 | Alternating | Auto |
| 20.0 | Gentle | 40.0 | 116.0 | 100 | 4 | Alternating | Auto |
| 21.0 | Gentle | 40.0 | 62.0 | 100 | 4 | Alternating | Auto |
| 22.0 | Gentle | 40.0 | 59.0 | 100 | 4 | Alternating | Auto |
| 23.0 | Gentle | 40.0 | 39.0 | 100 | 4 | Alternating | Auto |
| 24.0 | Gentle | 40.0 | 783.0 | 100 | 4 | Alternating | Auto |
| 25.0 | Gentle | 40.0 | 238.0 | 100 | 1 | Alternating | Auto |
| 26.0 | Gentle | 49.0 | 59.0 | 100 | 1 | Alternating | Auto |
| 27.0 | Gentle | 49.0 | 39.0 | 100 | 1 | Alternating | Auto |
| 28.0 | Gentle | 81.0 | 783.0 | 100 | 4 | Alternating | Auto |
| 29.0 | Gentle | 49.0 | 783.0 | 100 | 1 | Alternating | Auto, | wherein Seq is a number corresponding to a sequential step in the protocol, Waveshape is selected from among the group of waveshapes consisting of gentle, mild, sharp, and pulse waveslopes, Freq1 is a first frequency in hertz of an electrical signal applied to the first pair of electrodes, Freq2 is a second frequency in hertz of an electrical signal applied to the second pair of electrodes, Current is an amperage of the electrical signals in microamps, Duration is a time in minutes, Polarity is selected from among the group of polarities consisting of positive, negative, and alternating, and Mode is set to automatically perform the protocol.

19. The method of claim 2 wherein the protocol is for use in conjunction with orthodontic procedures and wherein the frequency of the electrical signals applied by the first pair of electrodes is programmed in a range of approximately 9.0 to 321 hertz and the amplitude is programmed in a range of approximately 20 to 400 microamps, and the frequency of the electrical signals applied by the second pair of electrodes is programmed in a range of approximately 0.1 to 783 hertz and the amplitude is programmed in a range of approximately 20 to 400 microamps.

20. The method of claim 19 wherein the protocol is for use in conjunction with prevention of pain due to orthodontic procedures and wherein the frequency of the electrical signals applied by the first pair of electrodes is programmed in a range of approximately 9.0 to 294 hertz and the amplitude is programmed in a range of approximately 20 to 400 microamps, and the frequency of the electrical signals applied by the second pair of electrodes is programmed in a range of approximately 45 to 783 hertz and the amplitude is programmed in a range of approximately 20 to 400 microamps.

21. The method of claim 20 wherein parameters for the protocol for prevention of pain due to orthodontic procedures have the following approximate values:

| Mode Code: 0090 | | Ortho - pain | | | Type: User | |
|---|---|---|---|---|---|---|
| Seq | Waveshape | Freq1 | Freq2 | Current | Duration | Polarity | Mode |
| 1.0 | Gentle | 18.0 | 62.0 | 100 | 3 | Alternating | Auto |
| 2.0 | Gentle | 18.0 | 396.0 | 100 | 2 | Positive | Auto |
| 3.0 | Gentle | 18.0 | 77.0 | 100 | 2 | Alternating | Auto |

-continued

| Mode Code: 0090 | | | Ortho - pain | | Type: User | |
|---|---|---|---|---|---|---|
| Seq | Waveshape | Freq1 | Freq2 | Current | Duration | Polarity | Mode |
| 4.0 | Gentle | 18.0 | 100.0 | 100 | 2 | Alternating | Auto |
| 5.0 | Gentle | 19.0 | 45.0 | 100 | 1 | Alternating | Auto |
| 6.0 | Gentle | 19.0 | 77.0 | 100 | 1 | Alternating | Auto |
| 7.0 | Gentle | 124.0 | 62.0 | 100 | 1 | Alternating | Auto |
| 8.0 | Gentle | 124.0 | 77.0 | 100 | 1 | Alternating | Auto |
| 9.0 | Gentle | 124.0 | 100.0 | 100 | 1 | Alternating | Auto |
| 10.0 | Gentle | 124.0 | 783.0 | 100 | 1 | Alternating | Auto |
| 11.0 | Gentle | 40.0 | 116.0 | 100 | 4 | Alternating | Auto |
| 12.0 | Gentle | 40.0 | 62.0 | 100 | 2 | Alternating | Auto |
| 13.0 | Gentle | 40.0 | 77.0 | 100 | 2 | Alternating | Auto |
| 14.0 | Gentle | 40.0 | 100.0 | 100 | 2 | Alternating | Auto |
| 15.0 | Gentle | 40.0 | 783.0 | 100 | 2 | Alternating | Auto |
| 16.0 | Gentle | 94.0 | 396.0 | 100 | 2 | Positive | Auto |
| 17.0 | Gentle | 40.0 | 396.0 | 100 | 2 | Positive | Auto |
| 18.0 | Gentle | 294.0 | 62.0 | 100 | 1 | Alternating | Auto |
| 19.0 | Gentle | 294.0 | 77.0 | 100 | 1 | Alternating | Auto |
| 20.0 | Gentle | 294.0 | 100.0 | 100 | 1 | Alternating | Auto |
| 21.0 | Gentle | 294.0 | 783.0 | 100 | 1 | Alternating | Auto |
| 22.0 | Gentle | 321.0 | 62.0 | 100 | 1 | Alternating | Auto |
| 23.0 | Gentle | 321.0 | 77.0 | 100 | 1 | Alternating | Auto |
| 24.0 | Gentle | 321.0 | 100.0 | 100 | 1 | Alternating | Auto |
| 25.0 | Gentle | 321.0 | 783.0 | 100 | 1 | Alternating | Auto |
| 26.0 | Gentle | 9.0 | 62.0 | 100 | 1 | Alternating | Auto |
| 27.0 | Gentle | 9.0 | 77.0 | 100 | 1 | Alternating | Auto |
| 28.0 | Gentle | 9.0 | 100.0 | 100 | 1 | Alternating | Auto |
| 29.0 | Gentle | 9.0 | 783.0 | 100 | 1 | Alternating | Auto |
| 30.0 | Gentle | 81.0 | 77.0 | 100 | 2 | Alternating | Auto |
| 31.0 | Gentle | 81.0 | 100.0 | 100 | 2 | Alternating | Auto |
| 32.0 | Gentle | 81.0 | 783.0 | 100 | 2 | Alternating | Auto |
| 33.0 | Gentle | 49.0 | 62.0 | 100 | 1 | Alternating | Auto |
| 34.0 | Gentle | 49.0 | 77.0 | 100 | 1 | Alternating | Auto |
| 35.0 | Gentle | 49.0 | 100.0 | 100 | 1 | Alternating | Auto |
| 36.0 | Gentle | 49.0 | 783.0 | 100 | 1 | Alternating | Auto |
| 37.0 | Gentle | 35.0 | 102.0 | 100 | 1 | Alternating | Auto, | wherein Seq is a number corresponding to a sequential step in the protocol, Waveshape is selected from among the group of waveshapes consisting of gentle, mild, sharp, and pulse waveslopes, Freq1 is a first frequency in hertz of an electrical signal applied to the first pair of electrodes, Freq2 is a second frequency in hertz of an electrical signal applied to the second pair of electrodes, Current is an amperage of the electrical signals in microamps, Duration is a time in minutes, Polarity is selected from among the group of polarities consisting of positive, negative, and alternating, and Mode is set to automatically perform the protocol.

22. The method of claim 19 wherein the protocol is for use in conjunction with orthodontic mid-adjustment procedures and wherein the frequency of the electrical signals applied by the first pair of electrodes is programmed in a range of approximately 40 to 284 hertz and the amplitude is programmed in a range of approximately 20 to 400 microamps, and the frequency of the electrical signals applied by the second pair of electrodes is programmed in a range of approximately 0.1 to 783 hertz and the amplitude is programmed in a range of approximately 20 to 400 microamps.

23. The method of claim 22 wherein parameters for the protocol for orthodontic mid-adjustment procedures have the following approximate values:

| Mode Code: 0091 | | | Ortho - mid adj | | Type: User | |
|---|---|---|---|---|---|---|
| Seq | Waveshape | Freq1 | Freq2 | Current | Duration | Polarity | Mode |
| 1.0 | Sharp | 58.0 | 0.1 | 100 | 1 | Alternating | Auto |
| 2.0 | Sharp | 58.0 | 1.0 | 100 | 1 | Alternating | Auto |
| 3.0 | Sharp | 58.0 | 2.0 | 100 | 1 | Alternating | Auto |
| 4.0 | Sharp | 58.0 | 32.0 | 100 | 1 | Alternating | Auto |
| 5.0 | Sharp | 40.0 | 116.0 | 100 | 4 | Alternating | Auto |
| 6.0 | Sharp | 40.0 | 100.0 | 100 | 4 | Alternating | Auto |
| 7.0 | Sharp | 40.0 | 59.0 | 100 | 4 | Alternating | Auto |
| 8.0 | Sharp | 40.0 | 39.0 | 100 | 4 | Alternating | Auto |
| 9.0 | Sharp | 40.0 | 783.0 | 100 | 4 | Alternating | Auto |
| 10.0 | Sharp | 40.0 | 238.0 | 100 | 1 | Alternating | Auto |
| 11.0 | Sharp | 284.0 | 100.0 | 100 | 2 | Alternating | Auto |
| 13.0 | Sharp | 284.0 | 59.0 | 100 | 2 | Alternating | Auto |
| 14.0 | Sharp | 284.0 | 39.0 | 100 | 2 | Alternating | Auto |
| 15.0 | Sharp | 284.0 | 783.0 | 100 | 2 | Alternating | Auto |
| 16.0 | Sharp | 284.0 | 238.0 | 100 | 1 | Alternating | Auto |
| 17.0 | Sharp | 91.0 | 100.0 | 100 | 1 | Alternating | Auto |
| 18.0 | Sharp | 91.0 | 783.0 | 100 | 3 | Alternating | Auto |
| 19.0 | Sharp | 81.0 | 100.0 | 100 | 2 | Alternating | Auto |
| 20.0 | Sharp | 81.0 | 783.0 | 100 | 2 | Alternating | Auto |
| 21.0 | Sharp | 49.0 | 100.0 | 100 | 1 | Alternating | Auto |
| 22.0 | Sharp | 49.0 | 59.0 | 100 | 1 | Alternating | Auto |
| 23.0 | Sharp | 49.0 | 39.0 | 100 | 1 | Alternating | Auto |
| 24.0 | Sharp | 49.0 | 783.0 | 100 | 1 | Alternating | Auto, | wherein Seq is a number corresponding to a sequential step in the protocol, Waveshape is selected from among the group of waveshapes consisting of gentle, mild, sharp, and pulse waveslopes, Freq1 is a first frequency in hertz of an electrical signal applied to the first pair of electrodes, Freq2 is a second frequency in hertz of an electrical signal applied to the second pair of electrodes, Current is an amperage of the electrical signals in microamps, Duration is a time in minutes, Polarity is selected from among the group of polarities consisting of positive, negative, and alternating, and Mode is set to automatically perform the protocol.

* * * * *